(12) United States Patent
Gonzalez et al.

(10) Patent No.: US 12,359,236 B2
(45) Date of Patent: Jul. 15, 2025

(54) PRODUCTION OF 2-HYDROXYACYL-CoAS AND DERIVATIVES THEREOF

(71) Applicant: Mojia Biotech Pte. Ltd., Singapore (SG)

(72) Inventors: Ramon Gonzalez, Tampa, FL (US); Alexander Chou, Houston, TX (US); James Clomburg, Houston, TX (US)

(73) Assignee: Mojia Biotech Pte. Ltd., Singapore (SG)

( * ) Notice: Subject to any disclaimer, the term of this patent is extended or adjusted under 35 U.S.C. 154(b) by 597 days.

(21) Appl. No.: 17/537,714

(22) Filed: Nov. 30, 2021

(65) Prior Publication Data
US 2022/0162661 A1    May 26, 2022

Related U.S. Application Data

(63) Continuation of application No. PCT/US2020/035827, filed on Jun. 3, 2020.

(60) Provisional application No. 62/856,934, filed on Jun. 4, 2019.

(51) Int. Cl.
*C12P 19/40*    (2006.01)

(52) U.S. Cl.
CPC ................... *C12P 19/40* (2013.01)

(58) Field of Classification Search
CPC ... C12P 19/40; C12P 7/42; C12N 9/88; C12Y 401/02
See application file for complete search history.

(56) References Cited

U.S. PATENT DOCUMENTS

| | | |
|---|---|---|
| 7,262,046 B2 | 8/2007 | Ka-Yiu et al. |
| 7,569,380 B2 | 8/2009 | Dittrich et al. |
| 8,129,157 B2 | 3/2012 | Gonzalez et al. |
| 8,691,552 B2 | 4/2014 | Gonzalez et al. |
| 8,795,991 B2 | 8/2014 | Bennett et al. |
| 8,962,272 B2 | 2/2015 | San et al. |
| 10,513,716 B2 | 12/2019 | Osterhout et al. |
| 2013/0031641 A1 | 1/2013 | Fisk et al. |
| 2013/0196359 A1 | 8/2013 | Siegel et al. |
| 2013/0316413 A1 | 11/2013 | Gonzalez et al. |
| 2014/0179942 A1 | 6/2014 | Finnegan |
| 2014/0256904 A1 | 9/2014 | Schaffer et al. |
| 2014/0273110 A1 | 9/2014 | Gonzalez et al. |
| 2019/0100741 A1 | 4/2019 | Gonzalez et al. |
| 2022/0112477 A1 | 4/2022 | Gonzalez et al. |

FOREIGN PATENT DOCUMENTS

| | | |
|---|---|---|
| CN | 103797109 A | 5/2014 |
| CN | 103857793 A | 6/2014 |
| EP | 3786290 A1 | 3/2021 |
| TW | 201420761 A | 6/2014 |
| WO | 2012/109176 A1 | 11/2013 |
| WO | 2016069929 A1 | 5/2016 |
| WO | 2017161041 A1 | 9/2017 |
| WO | 2017190056 A1 | 11/2017 |

OTHER PUBLICATIONS

Yan et al, Metabolic Engineering, vol. 61,2020, pp. 335-343, ISSN 1096-7176, doi.org/10.1016/j.ymben.2020.05.008. (Year: 2020).*
Robert J. Ouellette, J. David Rawn, 18—Aldehydes and Ketones, Editor(s): Robert J. Ouellette, J. David Rawn, Organic Chemistry Study Guide, Elsevier, 2015, pp. 313-333, ISBN 9780128018897, doi.org/10.1016/B978-0-12-801889-7.00018-2 (Year: 2015).*
Jenkins, B. et al., "Peroxisomal 2-Hydroxyacyl-CoA Lyase Is Involved in Endogenous Biosynthesis of Heptadecanoic Acid", Molecules, vol. 22, publication 1718, 2017, 1-6.
Kitamura, T. et al., "Phytosphingosine degradation pathway includes fatty acid α-oxidation reactions in the endoplasmic reticulum", PNAS, vol. 114, No. 13, 2017, E2616-E2623.
Macdonald, L. C. et al., "Engineering broad-spectrum digestion of polyuronides from an exolytic polysaccharide lyase", Biotechnol. Biofuels, vol. 9, publication 43, 2016, 1-14.
Macdonald,, M. C. et al., "Rhodotorula glutinis Phenylalanine/ Tyrosine Ammonia Lyase Enzyme Catalyzed Synthesis of the Methyl Ester of para-Hydroxycinnamic Acid and its Potential Antibacterial Activity", Frontiers in Microbiol., vol. 7, Article 281, 2016, 1-11.
Ramirez-Trujillo, J. et al., "The Sinorhizobium meliloti glyoxylate cycle enzyme isocitrate lyase (AceA) is required for the utilization of poly-ß-hydroxybutyrate during carbon starvation", Annals of Microbiol., vol. 66, 2016, 921-924.
Sriram, D. et al., "5-Nitro-2,6-dioxohexahydro-4-pyrimidinecarboxamides: synthesis, in vitro antimycobacterial activity, cytotoxicity, and isocitrate lyase inhibition studies", Journal of Enzyme Inhibition and Medicinal Chemistry, vol. 25, No. 6, 2010, 765-772.
Wiedner, R. et al., "Improving the Properties of Bacterial R-Selective Hydroxynitrile Lyases for Industrial Applications", Chem Cat Chem, vol. 7, 2015, 325-332.

(Continued)

*Primary Examiner* — Kade Ariani
(74) *Attorney, Agent, or Firm* — Elmore Patent Law Group, P.C.; Carolyn S. Elmore; Mahreen Chaudhry Hoda

(57) ABSTRACT

The production of substituted 2-hydroxyacyl-CoA molecules by a novel reaction is described. The reaction involves the condensation of formyl-CoA with a carbonyl-containing molecule. Such carbonyl-containing molecules include a substituted aldehyde and a ketone. The reaction is catalyzed by enzymes using a TPP-dependent mechanism. Also described is the production of unsubstituted and substituted 2-hydroxyacyl-CoA molecules comprising the condensation of formyl-CoA with a carbonyl-containing molecule, wherein the condensation is catalyzed by a prokaryotic HACL. The 2-hydroxyacyl-CoA can be converted to chemical products having broad applications by using enzyme catalysts. The combination of enzyme catalysts comprises novel biochemical reaction pathways that can be deployed either as polypeptides in a reaction buffer or genetically encoded in recombinant microorganisms.

27 Claims, 15 Drawing Sheets

(56) References Cited

OTHER PUBLICATIONS

Xu, R. et al., "Enzymatic enantioselective transcyanation of silicon-containing aliphatic ketone with (S)-hydroxynitrile lyase from Manihot esculenta", Appl. Microbiol. Biotechnol., vol. 66, 2004, 27-33.

Zhang, J. et al., "Biocatalytic Enantioselective Hydroaminations for Production of N-Cycloalkyl-Substituted L-Aspartic Acids Using Two C—N Lyases", Advanced Synthesis and Catalysis, vol. 361, No. 11, 2433-2437, 2019.

Casteels, et al., "The role of 2-hydroxyacyl-CoA lyase, a thiamin pyrophosphate-dependent enzyme, in the peroxisomal metabolism of 3-methyl-branched fatty acids and 2-hydroxy straight-chain fatty acids", Biochem Soc Transact, 35(5), Nov. 2007, 876-880.

Schuchmann, K., et al., "Direct and reversible hydrogenation of CO2 to formate by a bacterial ::arbon dioxide reductase", Science {New York, N.Y.), 342(6164), 2013, 1382-5.

International Search Report for parent case, App. No. PCT/US15/058121, Issued Mar. 11, 2016.

Uniprot List, KeGG, Aug. 9, 2020, pp. 1-4.

Cintolesi, A. et al., "In silico assessment of the metabolic capabilities of an engineered functional reversal of the beta-oxidation cycle for the synthesis of longer-chain (C>/=4) products", Metabolic Engineering, vol. 23, Feb. 22, 2014, 100-115.

Clomburg, J. M. et al., "Integrated engineering of beta-oxidation reversal and omegaoxidation pathways for the synthesis of medium chain omega-functionalized carboxylic acids", Metabolic Engineering, vol. 28, Jan. 28, 2015, 202-212.

Devos, Damien et al., "Practical Limits of Function Prediction", Proteins: Structure, Function, and Genetics, vol. 41, 2000, 98-107.

Fraccascia, P. et al., "Role of Thiamine Pyrophosphate in Oligomerisation, Functioning and Import of Peroxisomal 2-hydroxyacyl-CoA Lyase", Biochimica et Biophysica Acta., 1814(10), 2011, 1226-1233.

Hofmeister, A. et al., "(R)-Lactyl-CoA dehydratase from Clostridium propionicum", European Journal of Biochem. 206(2), 1992, 547-552.

Kim, S. et al., "Synthesis of medium-chain length (C6-C10) fuels and chemicals via betaoxidation reversal in *Escherichia coli*", Journal of Industrial Microbiology and Biotechnology, vol. 42, Feb. 3, 2015, 465-475.

Kisselev, Lev, "Polypeptide Release Factors in Prokaryotes and Eukaryotes: Same Function, Different Structure", Structure, vol. 10, Jan. 2002, 2002, 8-9.

Mannaerts, G. P. et al., "Peroxisomal lipid Degradation via beta- and alpha-oxidation in mammals", Cell Biochemistry and Biophysics, vol. 32, Dec. 31, 2000, 73-87.

Poehlein, et al., "An Ancient Pathway Combining Carbon Dioxide Fixation with the Generation and Utilization of a Sodium Ion Gradient for ATP Synthesis", PLoS One, vol. 7, No. 3, Mar. 29, 2012, e33439.

Tai, Y-S. et al., "C1 metabolism redesigned", Nature Chemical Biology, vol. 11, Jun. 2015, 384-386.

Tobimatsu, T. et al., "Heterologous Expression, Purification, and Properties of Diol Dehydratase, an Adenosylcobalamin-Dependent Enzyme of Klebsiella Oxytoca", Archives of Biochemistry and Biophysics, 347(1), 1997, 132-140.

Whisstock, James C. et al., "Prediction of protein function from protein sequence and structure", Quarterly Reviews of Biophysics, vol. 36 (3), 2003, 307-340.

Witkowski, Andrzej et al., "Conversion of a Beta-Ketoacyl Synthase to a Malonyl Decarboxylase by Replacement of the Active-Site Cysteine with Glutamine", Biochemistry, vol. 38, 1999, 1999, 11643-11650.

Chou, A., et al., "2-Hydroxyacyl-CoA lyase catalyzes acyloin condensation for one-carbon bioconversion", Nature Chemical Biology, Supplementary Information DOI: 10.1038/s41589-019-0328-0, 1-26, 2019.

Chou, A., et al., "2-Hydroxyacyl-CoA lyase catalyzes acyloin condensation for one-carbon bioconversion", Nature Chemical Biology, 15(9) DOI: 10.1038/S41589-019-0328-0, 900-906, 2019.

EC numbers from the Expasy Enzyme database archived Nov. 5, 2014 or the EC number 4.1.1 subclass.

EC numbers from the Expasy Enzyme database archived on Dec. 13, 2013 for the EC number 4.1.2 subclass.

Expasy Enzyme database (enzyme.expasy.org).

KEGG entries for 2-hydroxyacyl-CoA lyase and oxalyl-CoA-decarboxylase (each accessed on Sep. 12, 2024) Enzyme: 4.1.1.8.

KEGG entries for 2-hydroxyacyl-CoA lyase and oxalyl-CoA-decarboxylase (each accessed on Sep. 12, 2024) Enzyme: 4.1.2.63.

Mcdonald, A. G, et al., "Fifty-five years of enzyme classification: advances and difficulties", FEBS J, 281, 2014, 583-592.

Zhang, C., et al., "KEGG_Extractor: An Effective Extraction Tool for KEGG Orthologs", Genes, 14:386, 2023.

\* cited by examiner

PRODUCTION OF 2-HYDROXYACYL-CoAS AND DERIVATIVES THEREOF

RELATED APPLICATIONS

This application is a continuation International Application No. PCT/US20/35827, which designated the United States and was filed on Jun. 3, 2020, published in English, which claims the benefit of U.S. Provisional Application No. 62/856,934, filed on Jun. 4, 2019. The entire contents of the above-identified applications are herein incorporated by reference.

GOVERNMENT SUPPORT

This invention was made with government support under Grant No: CBET-1605999, awarded by the NSF. The government has certain rights in the invention.

FIELD OF THE INVENTION

The invention relates to the use of enzyme combinations or engineered microorganisms that can make various chemicals for industrial use. In particular, the production of chemicals through novel biochemical reaction pathways is described. These pathways involve a novel intermediate, specifically 2-hydroxyacyl-CoA with one or more substituent group, along with novel reactions for both its generation from different feedstocks and its conversion to different industrial chemicals.

BACKGROUND OF THE INVENTION

The biosynthesis of molecules with applications ranging from biofuels and green chemicals to therapeutic agents rely on reactions catalyzing the formation of carbon-carbon bonds. Serving as building blocks for these pathways, small precursor metabolites are subsequently condensed and modified until the desired chain length and functionality are achieved.

Naturally occurring, canonical metabolism relies mainly on the use of two or three carbon metabolites that serve as the building blocks for diverse biological chemistry. While these pathways have been exploited for the production of numerous chemical products, these approaches face limitations particularly in relation to the use of one-carbon substrates for chemical production. Existing approaches, for example, typically require first the production of two or three carbon metabolites from one-carbon substrates. Thus, there exists an opportunity to develop more direct routes to produce compounds using one carbon substrates.

One novel route for one carbon utilization is by the use of the enzyme 2-hydroxyacyl-CoA lyase (HACL), which has been discovered to catalyze a one-carbon elongation reaction for the condensation of formyl-CoA with aldehydes of varying chain length and produces unsubstituted/non-functionalized 2-hydroxyacyl-CoAs (described, for example, in WO2016/069929A1 and U.S. Pat. App. Pub. No. 20190100741A1). While this novel one-carbon elongation reaction enables an innovative platform for generating products from one-carbon substrates, the range of possible products is limited to those than can be derived from the unsubstituted/non-functionalized 2-hydroxyacyl-CoA intermediate. Herein, we describe novel routes to produce a greater variety of compounds based on the use of an acyloin condensation reaction between either a functionalized aldehyde or a ketone and formyl-CoA to form substituted/functionalized 2-hydroxyacyl-CoAs. Combined with various pathways for converting the substituted/functionalized 2-hydroxyacyl-CoAs to products of interest, along with pathways for generating required starting intermediates from different feedstocks, the use of this novel reaction catalyzed by enzymes such as HACL provides an innovative route for the production of a range of industrial chemicals.

SUMMARY OF THE INVENTION

This disclosure generally relates to the use of either enzyme combinations or recombinant microbes expressing those enzyme combinations to make chemical products by utilization of one carbon substrates. Chemical products are generally derived from a substituted/functionalized 2-hydroxyacyl-CoAs intermediate, generated by an acyloin condensation reaction between formyl-CoA and a substituted aldehyde or ketone (FIG. 1), with various enzymes/pathway combinations enabling the conversion of the substituted/functionalized 2-hydroxyacyl-CoA to a range of products (FIG. 2 and FIG. 3).

Several approaches are described herein. In one approach, the enzymes are made and combined in one or more in vitro reactions to make the desired products. In another approach, recombinant cells are harvested and used as temporary bioreactors containing the enzymes to do all or part of the reactions for as long as the enzymes remain active. In another approach, the cells are lysed and the lysate is used to catalyze the needed reactions. In yet another approach, recombinant cells are used in a growing, living system to continually make products. Combinations of the various approaches can also be used.

As described herein, the central reactions for the synthesis of these products are acyloin condensation reactions catalyzed by enzymes using a TPP-dependent mechanism. Examples of these enzymes include those named 2-hydroxyacyl-CoA lyase, oxalyl-CoA decarboxylase, or benzaldehyde lyase. Herein, we refer to this group of enzymes as TPP-dependent enzymes that catalyze acyloin condensation reactions or as "TPP-dependent enzymes" for simplicity. In this invention, the condensation reaction occurs between a formyl-CoA molecule and a substituted aldehyde, such as an aldehyde containing one or more additional functional group, or a ketone, resulting in 2-hydroxyacyl-CoA containing one or more substituent groups (also referred to herein interchangeably as a "substituted 2-hydroxyacyl-CoA" and "functionalized 2-hydroxyacyl-CoA") (FIG. 1). This condensation reaction serves as a platform for the synthesis of varied chemical products based on the structure of the substituted 2-hydroxyacyl-CoA and subsequent modification by a variety of metabolic pathways and enzymes for carbon rearrangement and the addition, removal, or modification of functional groups (FIG. 2 and FIG. 3).

One aspect of the invention is the generation of and production of products from a functionalized 2-hydroxyacyl-CoA. Condensation of a functionalized aldehyde with formyl-CoA using a TPP-dependent enzyme, such as HACL, results in the production of a functionalized 2-hydroxyacyl-CoA that can be further modified as desired (FIG. 2).

Another aspect of the invention is the production of branched molecules. Condensation of a ketone with formyl-CoA using a TPP-dependent enzyme, such as HACL, results in the production of an alkyl-branched 2-hydroxyacyl-CoA that can be further modified as desired (FIG. 3).

In one embodiment of the invention, the ketone is acetone. Condensation of the acetone with formyl-CoA results in the production of a 2-hydroxyisobutyryl-CoA.

In one embodiment, the alpha-branched 2-hydroxyacyl-CoA is converted to an alpha-branched 2-hydroxyaldehyde by an acyl-CoA reductase (ACR).

Another aspect of this disclosure relates to the production of poly-hydroxylated molecules. An aldehyde having one or more hydroxyl groups is condensed with formyl-CoA to produce a polyhydroxy-2-hydroxyacyl-CoA. The resulting molecule can be further modified as desired.

In one embodiment (FIG. 4), the polyhydroxy-2-hydroxyacyl-CoA is converted to a polyhydroxyaldehyde. The polyhydroxyaldehyde is suitable for further condensation with formyl-CoA to elongate the carbon backbone. This enables the synthesis of much longer products than the initial substrates.

In one embodiment, the product is a polyhydroxyaldehyde, for example aldoses such as glucose.

In one embodiment, the product is a polyhydroxycarboxylic acids, for example aldonic acids such as ascorbic acid.

In one embodiment, the product is a polyols, for example glycerol.

In one embodiment, the hydroxyaldehyde is produced by the HACL-catalyzed condensation of formaldehyde with formyl-CoA, resulting in glycolyl-CoA, which is further reduced to glycolaldehyde (2-hydroxyacetaldehyde). This enables product synthesis from solely one-carbon substrates. The condensation of formaldehyde with formyl-CoA to produce the hydroxyaldehyde can also be catalyzed other TPP-dependent enzymes.

In yet additional aspects, the present invention therefore also includes the identification of variants of HACL from prokaryotes and methods for the production of an unsubstituted or substituted 2-hydroxyacyl-CoA comprising contacting formyl-CoA and a carbonyl-containing compound with a prokaryotic HACL. As described below, while α-oxidation has been hypothesized to take place in prokaryotes, the existence of prokaryotic HACLs has not previously been confirmed. As such, the present invention encompasses methods for producing unsubstituted or substituted 2-hydroxyacyl-CoA comprising contacting formyl-CoA and a carbonyl-containing compound with a prokaryotic HACL and a recombinant microorganism comprising a DNA molecule encoding a prokaryotic HACL catalyzing the production of a unsubstituted or substituted 2-hydroxyacyl-CoA from formyl-CoA and a carbonyl-containing compound. In certain embodiments, the HACL is Rhodospirillales bacterium URHD0017 HACL (RuHACL). In yet additional aspects, the HACL is G390N RuHACL.

The processes described herein can involve performing traditional fermentations using industrial organisms (for example bacteria or yeast, such as E. coli, B. subtilus, S. cerevisiae, P. pastoris and the like) that convert desired feedstocks, including single carbon compounds such as methane, methanol, formate, or carbon dioxide, into chemical products. These organisms are considered workhorses of modern biotechnology, and methods of genetically engineering, and scaling up for industrial production levels are well-known to those of skill in the art. Media preparation, sterilization, inoculum preparation, fermentation, and product recovery from the cells, or the medium, or both, are the main steps of the process.

The microorganisms can be used as living chemical manufacturing systems, or can be harvested and used as bioreactors for as long as the enzymes remain functional in the non-growing cells. Alternatively, the enzymes, from lysed cell extract or in purified form, can be used in an in vitro system reconstituted from the various individual enzymes. In certain cases, such an embodiment may be preferred as allowing the most control over product synthesis. However, in other cases, living systems may be preferred due to a number of advantages and for specific applications.

The pathways in a living system are generally made by transforming the microbe with an expression vector encoding one or more of the proteins, but the genes can also be added to the chromosome by recombineering, homologous recombination, and similar techniques. Where the needed protein is endogenous, as is the case in some instances, it may suffice as is, but it is often overexpressed using an inducible promoter for better functionality and user-control over the level of active enzyme.

Reference to proteins herein can be understood to include reference to the gene encoding such protein. Thus, a claimed "permease" can include the related gene encoding that permease. However, it is preferred herein to refer to the protein by standard name per ecoliwiki.net or Human Genome Organisation (HUGO) since both enzymatic and gene names have varied widely, especially in the prokaryotic arts.

Once an exemplary protein is obtained, many additional examples of proteins with similar activity can be identified by BLAST search. Further, every protein record is linked to a gene record, making it easy to design overexpression vectors. Many of the needed enzymes are already available in vectors and can often be obtained from cell depositories or from the researchers who cloned them. But, if necessary, new clones can be prepared based on available sequence information using e.g., RT-PCR techniques or de novo gene synthesis. Thus, it should be easily possible to obtain all of the needed enzymes for overexpression.

Another way of finding suitable enzymes/proteins for use in the invention is to consider other enzymes with the same EC number, since these numbers are assigned based on the reactions performed by a given enzyme. An enzyme can thus be obtained, e.g., from AddGene.org or from the author of the work describing that enzyme, and tested for functionality as described herein. In addition, many sites provide lists of proteins that all catalyze the same reaction. See e.g., BRENDA, UNIPROT, ECOPRODB, ECOLIWIKI, to name just a few.

Understanding the inherent degeneracy of the genetic code allows one of ordinary skill in the art to design multiple nucleotide sequences that encode the same amino acid sequence. NCBI™ provides codon usage databases for optimizing DNA sequences for protein expression in various species. Using such databases, a gene or cDNA may be "optimized" for expression in E. coli, yeast, algal or other species using the codon bias for the species in which the gene will be expressed.

Initial cloning experiments have proceeded in E. coli for convenience since most of the required genes are already available in plasmids suitable for bacterial expression, but the addition of genes to bacteria is of nearly universal applicability. Indeed, since recombinant methods were invented in the 1970's and are now so commonplace, even school children perform genetic engineering experiments using bacteria. Such species include e.g., Bacillus, Streptomyces, Azotobacter, Rhizobium, Pseudomonas, Micrococcus, Nitrobacter, Proteus, Lactobacillus, Pediococcus, Lactococcus, Salmonella, Streptococcus, Paracoccus, Vibrio, Corynebacterium, Methanosarcina, Methylococcus, Methylobacterium, Methylomicrobium, Synechococcus, Rhodobacter or any of the completely sequenced bacterial species.

Indeed, hundreds of bacterial genomes have been completely sequenced, and this information greatly simplifies both the generation of vectors encoding the needed genes, as well as the planning of a recombinant engineering protocol. Such species are listed along with links at en.wikipedia.org/wiki/List of sequenced bacterial genomes.

Additionally, yeast, such as *Saccharomyces* are common species used for microbial manufacturing, and many species can be successfully engineered with heterologous metabolic pathways for product synthesis. Other species include but are not limited to *Candida, Arxula adeninivorans, Candida boidinii, Hansenula polymorpha (Pichia angusta), Kluyveromyces lactis, Pichia pastoris,* and *Yarrowia lipolytica*, to name a few.

It is also possible to genetically modify many species of algae, including e.g., *Spirulina, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira, Botryococcus* and *Laminaria japonica*. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Non-limiting examples of microorganisms that can be used include *Escherichia coli, Saccharomyces cerevisiae, Bacillus methanolicus, Pichia pastoris, Candida boidinii, Pseudomonas putida, Methylococcus capsulatus, Methylobacterium extorquens, Methylomicrobium buryatense, Corynebacterium glutamicum, Clostridium autoethanogenum,* and *Clostridium ljungdahlii*.

Furthermore, a number of databases include vector information and/or a repository of vectors and can be used to choose vectors suitable for the chosen host species. See, for example, AddGene.org which provides both a repository and a searchable database allowing vectors to be easily located and obtained from colleagues. See also Plasmid Information Database (plasmid.med.harvard.edu) and DNASU.org having over 191,000 plasmids. A collection of cloning vectors of *E. coli* is also kept at the National Institute of Genetics as a resource for the biological research community.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ expression plasmids hosting multigene operons or 2 or more open reading frames (ORFs) encoding the needed genes for convenience, but it may be preferred to insert operons or individual genes into the genome for long term stability.

Still further improvements in yield can be had by reducing competing pathways, such as those pathways for making e.g., acetate, formate, ethanol, and lactate, and it is already well known in the art how to reduce or knockout these pathways.

As used herein, "homolog" means an enzyme with at least 40% identity to one of the listed sequences and also having the same general catalytic activity, although kinetic parameters of the reactions can of course vary. While higher identity (for example, at least 60%, 70%, 80%, 90%, or 95% and the like) may be preferred, it is typical for bacterial sequences to diverge significantly (40-60% identity), yet still be identifiable as homologs, while mammalian species tend to diverge much less (80-90% identity). Unless specified otherwise, any reference to an enzyme herein also includes its homologs that catalyze the same reaction.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova TA & Madden TL (1999) FEMS Microbiol. Lett. 174:247-250, and available through the NCBI website. The default parameters were used, except the filters were turned OFF. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 1 1 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W word size [Integer] default=1 1 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at NCBI™ (ncbi.nlm.nih.gov/BLAST/).

As used herein, references to cells or bacteria or strains and all such similar designations include progeny thereof. The use of the singular "cell" does not imply that a single cell is to be used in any method, but includes all progeny produced by growing such cell. It is also understood that all progeny may not be precisely identical in DNA content, due to deliberate or inadvertent mutations that have been added to the parent. Mutant progeny that have the same function or biological activity as screened for in the originally transformed cell are included. Where distinct designations are intended, it will be clear from the context.

The terms "operably associated" or "operably linked," as used herein, refer to functionally coupled nucleic acid sequences.

As used herein "recombinant" or "engineered" is relating to, derived from, or containing genetically engineered material. In other words, the genome was intentionally manipulated by humans in some way.

"Reduced activity" or "inactivation" (indicated by "−") is defined herein to be at least a 75% reduction in protein activity, as compared with an appropriate control species. Preferably, at least 80, 85, 90, 95% reduction in activity is attained, and in the most preferred embodiment, the activity is eliminated (100%, aka a "knock-out" or "null" mutants, indicated by Δ). Proteins can be inactivated with inhibitors, by mutation, or by suppression of expression or translation, and the like. Use of a frame shift mutation, early stop codon, point mutations of critical residues, or deletions or insertions, and the like, can completely inactivate (100%) gene product by completely preventing transcription and/or translation of active protein.

"Overexpression" or "overexpressed" (indicated by "+") in a cell is defined herein to be at greater expression than in the same cell without the genetic modification. Preferably, it is at least 150% of protein activity as compared with an appropriate control species, and preferably 200, 500, 1000%) or more, or any activity in a host that would otherwise lack that enzyme. Overexpression can be achieved by mutating the protein to produce a more active form or a form that is resistant to inhibition, by removing inhibitors, by adding activators, and the like. Overexpression can also be achieved by removing repressors, adding multiple copies of the gene to the cell, or upregulating the endogenous gene, and the like.

The term "endogenous" or "native" means that a gene originated from the species in question, without regard to subspecies or strain, although that gene may be naturally or intentionally mutated. Thus, genes from Clostridia would not be endogenous to *Escherichia*, but genes from *E. coli* would be considered to be endogenous to any species of *Escherichia*. By contrast, the term "wild type" means a functional native gene that is not modified from its form in the wild. "Heterologous" means the gene is from a different biological source (microbe, plant, or animal). "Heterologous" may also refer to an endogenous gene removed from its normal milieu, for example on a plasmid or inserted into the chromosome at a location other than its normal location. In these cases, the gene may be expressed either from its native promoter or from a heterologous promoter.

"Expression vectors" are used in accordance with the art-accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expression vectors also exist and either can be used.

As used herein, "inducible" means that gene expression can be controlled by the hand-of-man, by adding e.g., a ligand to induce expression from an inducible promoter. Exemplary inducible promoters include the lac promoter, inducible by isopropylthio-β-D-galactopyranoside (IPTG), the yeast AOX1 promoter inducible with methanol, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressible, either inducibly or constitutively.

The use of the word "a" or "an", including when used in conjunction with the term "comprising." in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, background mutations that do not effect the invention, and the like.

As used herein, "substituted 2-hydroxyacyl-CoA" refers to a 2-hydroxyacyl-CoA having one or more hydrogens in the parent acyl molecule replaced by another atom or group of atoms, also known as a substituent group. Non-limiting examples of substituent groups include oxo, hydroxyls, carboxyls, alkyls, alkenyls, alkynyls, or amines.

As used herein, a "carbonyl-containing molecule" or "carbonyl-containing compound" refers to a molecule containing a functional group comprised of a carbon atom double-bonded to an oxygen atom. Non-limiting examples of these molecules include aldehydes and ketones. In certain aspects, the carbonyl-containing compound is not an unsubstituted aldehyde. In additional aspects, the carbonyl-containing compound is a substituted aldehyde or a ketone.

As described herein certain TPP-dependent enzymes catalyze the formation of a 2-hydroxyacyl-CoA from the acyloin condensation of a carbonyl-containing molecule, such as an aldehyde or ketone, with formyl-CoA using a TPP-dependent mechanism. Examples of these enzymes include those named 2-hydroxyacyl-CoA lyase, oxalyl-CoA decarboxylase, or benzaldehyde lyase. Generally, the condensation reaction occurs between a carbonyl-containing molecule and a formyl-CoA molecule, resulting in a molecule one carbon longer than the original carbonyl-containing compound.

As used herein, "carbon dioxide reductase" (EC 1.2.1.2), catalyzes the formation of formate from carbon dioxide ($CO_2$).

As used herein, "formate kinase" (EC 2.7.2.6), catalyzes the formation of formyl-phosphate from formate.

As used herein, "phosphate formyl-transferase" (EC 2.3.1.8), catalyzes the formation of formyl-CoA from formyl-phosphate.

As used herein, "acyl-CoA synthetase" (EC 6.2.1.-), catalyzes the formation of an acyl-CoA from a respective carboxylic acid or associated anion (e.g. formic acid or formate).

A "synthase" is a generic term that describes an enzyme that catalyzes the synthesis of a biological compound without the requirement of a nucleoside triphosphate, such as ATP, as co-substrate. A "synthetase" catalyzes the synthesis of a biological compound and requires ATP or another nucleoside triphosphate cosubstrate. "Ligase" is a term that describes an enzyme that catalyzes condensation of biological molecules optionally with simultaneous cleavage of ATP or other high energy substrate. However, in the scientific literature the terms "synthase", "synthetase", and "ligase" do not always follow these strict definitions. Accordingly, as used herein, these terms may be used interchangeably.

As used herein, "methane monooxygenase" (EC 1.14.13.25; 1.14.18.3), catalyzes the formation of methanol from methane.

As used herein, "methanol dehydrogenase" (EC 1.1.1.244; 1.1.2.7; 1.1.99.37), catalyzes the formation of formaldehyde from methanol.

As used herein, "acyl-CoA reductase" or "acylating aldehyde dehydrogenase" (EC 1.2.1.10), catalyzes the formation of an acyl-CoA from a respective aldehyde (e.g. formaldehyde) or the reverse.

As used herein, "thioesterase" (EC 3.1.2.-), catalyzes the formation of a carboxylic acid from a respective acyl-CoA.

As used herein, "alcohol dehydrogenase" (EC 1.1.1.-), catalyzes the conversion of an aldehyde functional group to an alcohol.

The following is a non-exhaustive list of examples of some of the key enzymes that can be used in the methods or expressed by the microorganisms described herein.

| Enzyme | Encoding gene(s) | Source | Accession No. |
| --- | --- | --- | --- |
| 2-hydroxyacyl-CoA lyase (HACL) | hacl1 | *Homo sapiens* | UniProt: Q9UJ83 |
| | hacl2 | *Homo sapiens* | UniProt: A1L0T0 |
| | hacl | *Rhodospirillales bacterium* URHD0017 | UniProt: A0A1H8YFL8 |
| | hacl | *Rhodospirillales bacterium* TMED256 | UniProt: A0A1Z9SHR5 |
| | hacl1 | *Rattus norvegicus* | UniProt: Q8CHM7 |
| | hacl1 | *Dictyostolium discoideum* | UniProt: Q54DA9 |
| | hacl1 | *Mus musculus* | UniProt: Q9QXE0 |
| | oxc | *Oxalobacter formigenes* | UniProt: P40149 |
| | oxc | *Escherichia coli* | UniProt: P0AFI0 |
| Carbon dioxide reductase | fdhF2, hycB2, hycB3, hydA2 | *Acetobacterium woodii* | YP_005268502.1, YP_005268503.1, YP_005268505.1, YP_005268506.1 |
| Formate kinase | ackA | *Salmonella typhymurium* | UniProt: P63411 |
| | ackA | *Escherichia coli* | NP_416799.1 |
| Phosphate formyl-transferase | eutD | *Escherichia coli* | NP_416953.1 |
| | pta | *Escherichia coli* | NP_416800.1 |
| | pduL | *Salmonella typhymurium* | UniProt: Q9XDN5 |
| Acyl-CoA synthase | acs | *Escherichia coli* | NP_418493.1 |
| Methane monooxygenase | mmoXYZBC, orfY | *Methylosinus trichosporium* OB3b | UniProt: 27353, P27354, P27355, Q53563, P27356, Q53562 |
| | mmoXYZBC, orfY | *Methylococcus capsulatus* Bath | UniProt: P22869, P18798, P11987, P18797, P22868, P22867 |
| Methanol dehydrogenase | mdh | *Bacillus methanolicus* | UniProt: P31005 |
| | mdo | *Mycobacterium* sp. DSM 3803 | UniProt: C5MRT8 |
| | moxF, moxI | *Methylobacterium extorquens* | UniProt: P16027, P14775 |
| Acyl-CoA reductase (acylating aldehyde dehydrogenase) | orf1179 | *Listeria monocytogenes* | UniProt: Q8Y7U1 |
| | eutE | *Salmonella typhymurium* | UniProt: P41793 |
| | ald | *Clostridium beijerinckii* | UniProt: Q71688 |
| | mhpF | *Escherichia coli* | UniProt: P77580 |
| | dmpF | *Pseudomonas* sp. strain CF600 | Uniprot: Q52060 |

The following abbreviations are used herein:

| ABBREVIATION | TERM |
| --- | --- |
| ATP | adenosine triphosphate |
| BSTFA | N,O-Bis(trimethylsilyl)trifluoroacetamide |
| C1 | One-carbon |
| CoA | coenzyme A |
| HACL | 2-hydroxyacyl-CoA lyase |
| ACR | Acyl-CoA reductase |
| IPTG | isopropyl-β-D-thiogalactopyranoside |

This summary is provided to introduce a selection of concepts that are further described below in the detailed description. This summary is not intended to identify key or essential features of the invention or claimed subject matter, nor is it intended to be used as an aid in limiting the scope of the claimed subject matter.

DETAILED DESCRIPTION OF THE INVENTION

Figure 1:
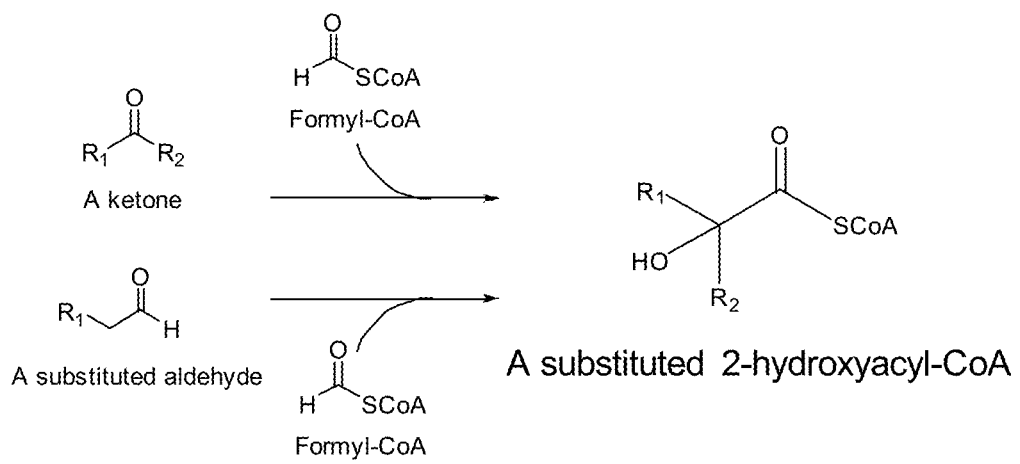
FIG. 1. Schematic of the novel condensation reaction resulting in the production of a substituted 2-hydroxyacyl-CoA by the condensation of formyl-CoA with either a ketone or a substituted aldehyde.

Biological reactions that enable carbon chain elongation via the addition of 2-5 carbon units to a carbon backbone, such as those found in the fatty acid, polyketide, and isoprenoid biosynthesis pathways, have been exploited for chemical production with applications ranging from pharmaceutical to industrial and agricultural. This has been possible largely due to their prevalence, universality of their cofactors, and versatility of their enzymes with respect to their substrates. Biological C1 addition reactions, on the other hand, are typically more complex and do not lend themselves to the same level of tractability, often requiring specific acceptor molecules or complex cofactors, making identification or engineering of efficient biocatalysts for C1 bioconversion difficult. For example, the Calvin-Benson-Bassham ($CO_2$ utilization/autotrophy) and ribulose monophosphate (formaldehyde utilization/methylotrophy) pathways employ ribulose phosphates as C1 acceptors, requiring the challenging task of engineering catalytic cycles that balance C1 utilization with competing pentose phosphate metabolism. Other pathways, such as the Wood-Ljungdahl pathway and serine cycle, make use of the specialized C1 carrier molecule tetrahydrofolate, for which the set of known C1-tetrahydrofolate acceptors limits its implementation, for example to glycine. Furthermore, these pathways result in the production of 2-3 carbon central metabolites, which must be in turn diverted to products of interest by further engineering. The latter results in problematic cross-talk between product-forming and growth-sustaining functions that compete for the same carbon and energy carriers, thus making the engineering of said pathways very challenging.

In an attempt to identify alternative, non-natural routes for C1 metabolism, we have examined the mammalian α-oxidation pathway, which results in the degradation of fatty acids by a C1 unit using the thiamine pyrophosphate (TPP) dependent enzyme 2-hydroxyacyl-CoA lyase (HACL). Encouraged by the reversible nature of TPP dependent enzymes and the favorable reaction thermodynamics, we hypothesized that HACL could act reversibly to catalyze a C1 addition reaction ligating formyl-CoA with an aldehyde using a TPP-dependent acyloin condensation mechanism. While formyl-CoA is not known to participate in any biosynthetic reaction or pathway, its use as a C1 extender unit to generate acyl-CoA products is an attractive characteristic of the proposed reaction given the set of biochemical conversions that can be performed on the resulting 2-hydroxyacyl-CoAs. This feature enables direct routes to wide-ranging product functionalities, representing a significant departure from the aforementioned established methods for C1 addition, which use more specialized prosthetic groups and result in molecules that must be rearranged through central metabolism prior to product synthesis. Through this approach, we have previously demonstrated the reversible nature of this thiamine pyrophosphate (TPP) dependent and the utility of this reaction for product synthesis from C1 substrates, including the use of 2-hydroxyacyl-CoA lyase HACL1 from *Homo sapiens* for the condensation of various chain length aldehydes with formyl-CoA. This specific C1 bioconversion pathway has been described in detail, for example, in WO2016/069929A1 and U.S. Pat. App. Pub. No. US20190100741A1, titled SYNTHETIC PATHWAY FOR BIOSYNTHESIS FROM 1-CARBON COMPOUNDS, the contents of which are expressly incorporated by reference herein.

The initial design of this C1 bioconversion platform using an enzyme, such as 2-hydroxyacyl-CoA lyase, employing the TPP-dependent acyloin condensation mechanism was based on the condensation of an unsubstituted aldehyde such as formaldehyde, acetaldehyde, propionaldehyde, etc. with a C1 unit in the form of formyl-CoA. By contrast, the current invention utilizes functionalized/substituted aldehydes and ketones as the substrate for condensation with formyl-CoA resulting in a functionalized/substituted 2-hydroxyacyl-CoA molecule that is one carbon longer than the original carbonyl-containing compound (FIG. 1). This condensation reaction serves as a platform for the synthesis of varied chemical products based on the structure and functionalization of the original aldehyde or ketone molecule as well as subsequent modification by a variety of metabolic pathways and enzymes for carbon rearrangement and the addition, removal, or modification of functional groups.

Figure 2:
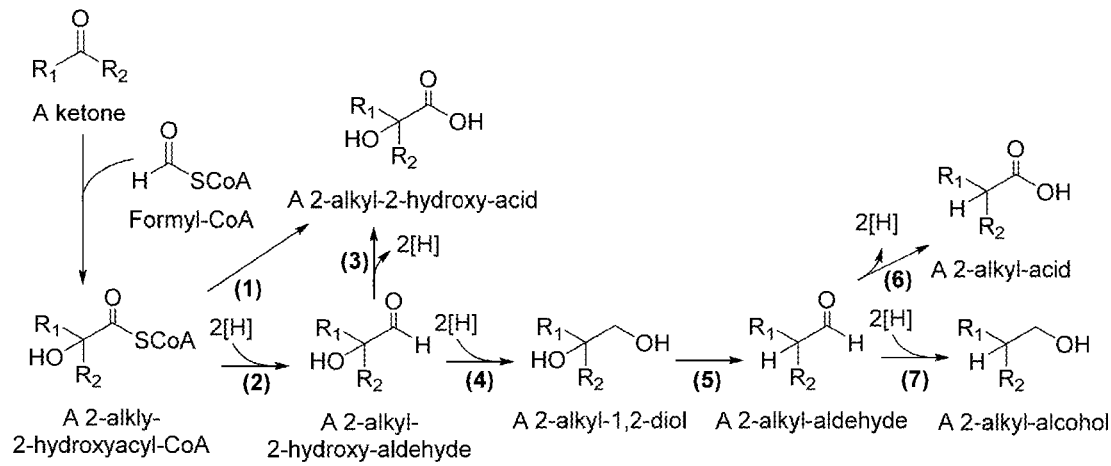
FIG. 2. 2-hydroxyacyl-CoA lyase catalyzed condensation of a ketone and formyl-CoA enables the production of 2-alkyl branched products. The 2-alkyl-2-hydroxyacyl-CoA generated via HACL mediated condensation and be converted into various products through various enzyme combinations. Numbers correspond to enzyme classes: 1) thioesterase; 2) acyl-CoA reductase; 3) aldehyde dehydrogenase; 4) 1,2-diol oxidoreductase; 5) diol dehydratase; 6) alcohol dehydrogenase. Exemplary products shown when the exemplary ketone substrate is acetone.

As described herein, a diverse range of functionalized/substituted aldehydes and ketones are condensed with formyl-CoA using the aforementioned enzyme(s) to produce functionalized/substituted 2-hydroxyacyl-CoAs extended by one carbon (FIG. 1). For example, in one embodiment where the carbonyl-containing molecule is a ketone, condensation of the ketone with formyl-CoA results in the production of a 2-alkyl branched product. One exemplary product is 2-hydroxyisobutyric acid, produced as a result of condensation of acetone and formyl-CoA to produce 2-hydroxyisobutyryl-CoA (FIG. 2). 2-hydroxyisobutyryl-CoA can be hydrolyzed to 2-hydroxyisobutyric acid by a thioesterase (FIG. 2).

The condensation of ketones of varying chain length, e.g., acetone, 2-butanone, 2-pentanone, 3-pentanone, with formyl-CoA enables the production of additional 2-alkyl branched products. Furthermore, as this condensation generates a 2-alkyl branched product, additional functional groups present in the initial ketone will remain as part of the 2-alkyl-2-hydroxyacyl-CoA intermediate formed and in associated products. For example, the use of hydroxyacetone would result in the formation of 2,3-dihydroxyisobutyryl-CoA following condensation with formyl-CoA, an intermediate that can undergo the various enzymatic reactions demonstrated for 2-hydroxyisobutyryl-CoA (FIG. 2) to form a range of products retaining the functional group present in the initial ketone. Ketones for TPP-dependent enzyme catalyzed or HACL catalyzed condensation with formyl-CoA can be added exogenously to reaction mixtures containing the required enzymes or to media supporting recombinant cells for the production of targeted products. Furthermore, ketones can be generated from unrelated carbon sources, e.g. glucose, glycerol, through common metabolic intermediates via engineering of various metabolic pathways (Cheong et al., 2016; Clomburg et al., 2012; Goh et al., 2014; Park et al, 2012; Srirangan et al., 2016). In addition, metabolic intermediates feeding ketone producing pathways can be generated through one-carbon substrate utilizing pathways, including those based on the TPP-dependent acyloin condensation of an unsubstituted aldehyde with a C1 unit in the form of formyl-CoA (see, for example, WO2016/069929A1 and U.S. Pat. App. Pub. No. 20190100741A1).

Figure 3:
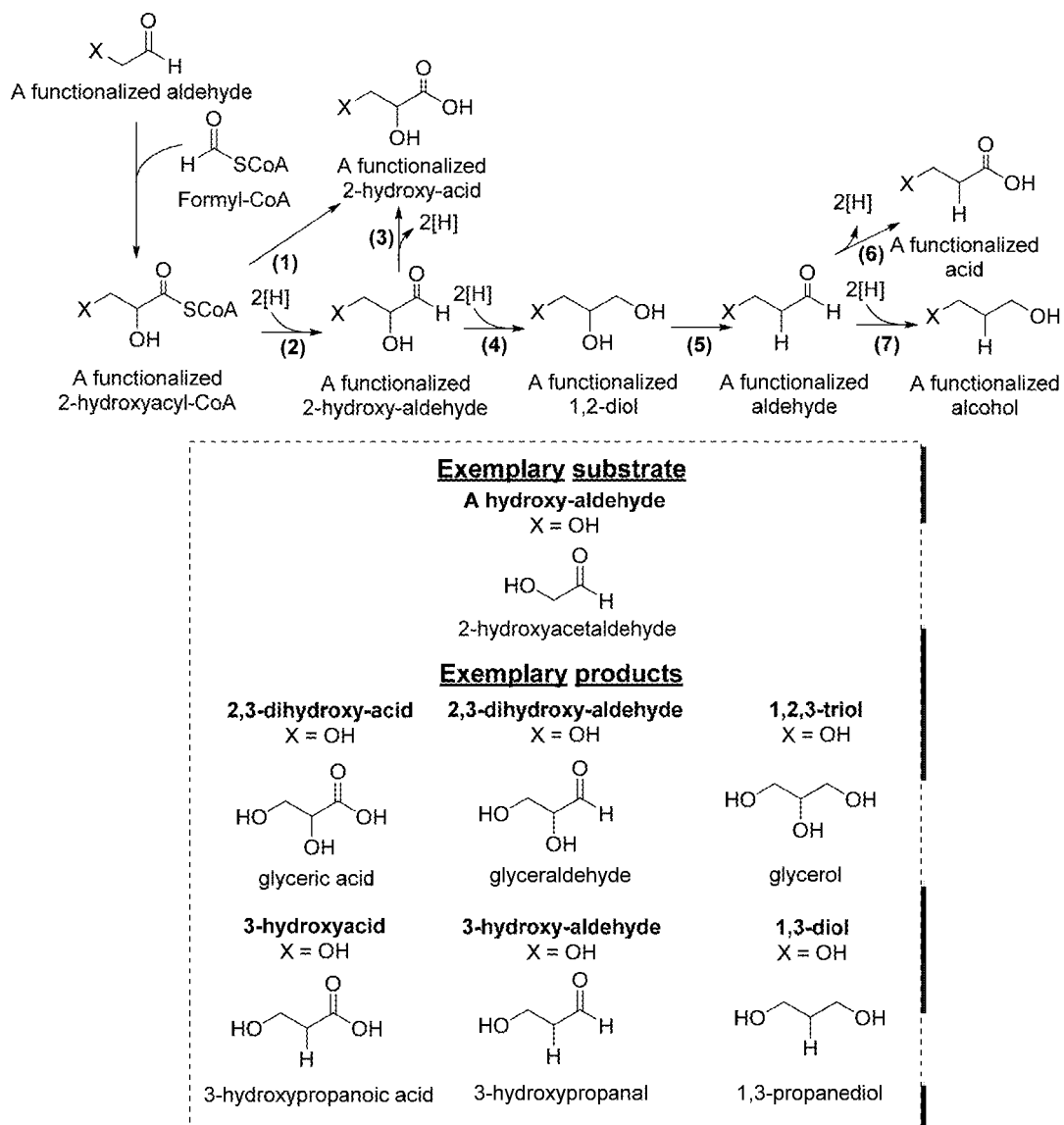
FIG. 3. 2-hydroxyacyl-CoA lyase catalyzed condensation of a functionalized aldehyde and formyl-CoA enables the production of chemical products with increased functionality compared to the use of an unsubstituted aldehyde. The functionalized 2-hydroxyacyl-CoA generated via HACL mediated condensation and be converted into various products through various enzyme combinations. Numbers correspond to enzyme classes: 1) thioesterase; 2) acyl-CoA reductase; 3) aldehyde dehydrogenase; 4) 1,2-diol oxidoreductase; 5) diol dehydratase; 6) alcohol dehydrogenase. Exemplary products shown when the exemplary functionalized aldehyde substrate is glycolaldehyde (2-hydroxyacetaldehyde).

In another embodiment, condensation of a functionalized aldehyde with formyl-CoA results in the production of a 2-hydroxyacyl-CoA containing the functionalization of the initial aldehyde (FIG. 3). One exemplary product is glyceric acid, produced as a result of the condensation of glycolaldehyde (2-hydroxy-acetaldehyde) and formyl-CoA to produce glyceryl-CoA (2,3-dihydroxypropionyl-CoA) (FIG. 3). Glyceryl-CoA can be hydrolyzed to glyceric acid by a thioesterase (FIG. 3).

The condensation of aldehydes with various functional groups, e.g. 2-hydroxy-acetaldehyde, 2-amino-acetaldehyde, 2-oxoacetic acid (glyoxylic acid), enables the production of 2-hydroxyacyl-CoA retaining the functional group(s) associated with the initial functionalized aldehyde. For example, the use of 2-amino-acetaldehyde results in the formation of 3-amino-2-hydroxypropionyl-CoA following condensation with formyl-CoA, an intermediate that can undergo the various enzymatic reactions demonstrated for glyceryl-CoA (FIG. 3) to form a range of products retaining the functional group present in the initial functionalized aldehyde. Furthermore, aldehydes of longer chain length and varying or multiple functional groups can also serve as the functionalized aldehyde for condensation with formyl-CoA. Functionalized aldehydes for the TPP-dependent enzyme catalyzed or HACL catalyzed condensation with formyl-CoA can be added exogenously to reaction mixtures containing the required enzymes or to media supporting recombinant cells for the production of targeted products. Furthermore, functionalized aldehydes can be generated from unrelated carbon sources, e.g. glucose, glycerol, through various metabolic pathways (Kunjapur and Prather, 2015; Lindlbauer et al., 2017; Rodriguez and Atsumi, 2012). In addition, functionalized aldehydes can be generated through one-carbon substrate utilizing pathways, including those based on the TPP-dependent acyloin condensation of an unsubstituted aldehyde with a C1 unit in the form of formyl-CoA (see, for example, WO2016/069929A1 and U.S. Pat. App. Pub. No. 20190100741A1).

Figure 4:
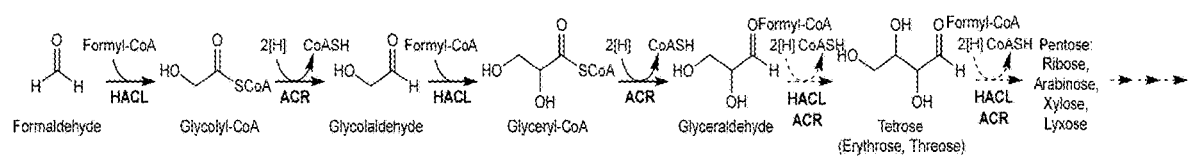
FIG. 4. Iterative elongation of a carbon backbone comprised of aldehydes and hydroxyaldehydes, referred to as aldose elongation. Elongation proceeds by the iterative action of an acyl-CoA reductase and a 2-hydroxyacyl-CoA lyase.

Another aspect of this disclosure relates to the iterative elongation of a carbon backbone by one carbon units. A carbonyl-containing molecule, once condensed with formyl-CoA to produce a 2-hydroxyacyl-CoA, is converted back into a form containing a carbonyl functional group. This molecule can then undergo further condensation with formyl-CoA. In one embodiment, the carbonyl-containing molecule is a hydroxyaldehyde. Following condensation with formyl-CoA, the resulting 2-hydroxyacyl-CoA is converted into a 2-hydroxyaldehyde, which can be further condensed with formyl-CoA. The result of this process is the production of polyhydroxyaldehydes, for example aldoses such as glucose; or polyhydroxycarboxylic acids, for example, aldonic acids such as ascorbic acid; or polyols, for example, glycerol (FIG. 4).

Figure 5:
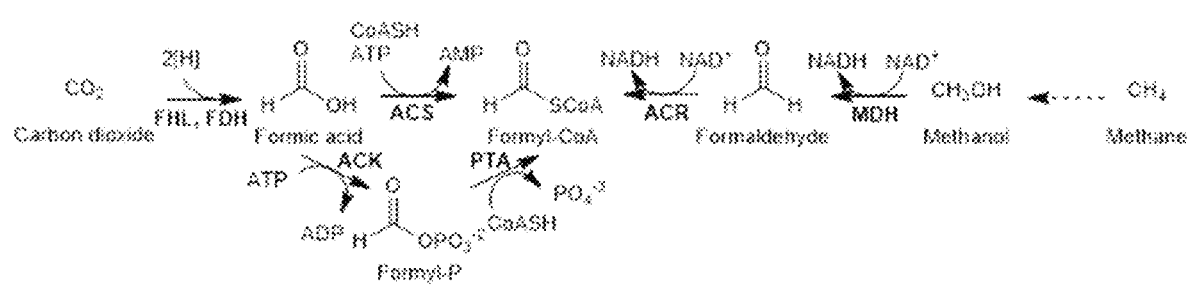
FIG. 5. Routes for the production of formyl-CoA from one-carbon substrates.

When combined with enzymes for the interchange and conversion of various C1 substrates, such as methane, methanol, formate, formaldehyde, and carbon dioxide, to formyl-CoA (FIG. 5) the designs described herein provide a novel platform for the conversion of C1 substrates to a variety of multi-carbon chemical products.

Enzymes of interest can be expressed from vectors such as pETDuet-1, pCDFDuet-1, or pRSFDuet-1 (Novagen, Darmstadt, Germany), which make use of the DE3 expression system. Genes can be codon optimized according to the codon usage frequencies of the host organism and synthesized by a commercial vendor or in-house. However, thousands of expression vectors and hosts are available, and this is a matter of convenience.

The genes can be amplified by PCR using primers designed with 15-22 base pairs of homology for the appropriate vector cut site. For enzymes that will not require a 6×-histadine tag fusion for purification, pCDFDuet-1 can be linearized with NcoI and EcoRI. Enzymes that will be purified by Ni-NTA column will make use of the 6×-HIS tag in pCDFDuet-1. The vector can be linearized using only EcoRI in this case. The PCR product can be inserted into the vector using e.g., the In-Fusion HD EcoDry Cloning System and the vector transformed by heat shock into competent E. coli cells. Transformants can be selected on solid media containing the appropriate antibiotic. Plasmid DNA can be isolated using any suitable method, including QIAprep Spin Miniprep Kit (Qiagen, Limburg), and the construct confirmed by PCR and sequencing. Confirmed constructs can be transformed by e.g., electroporation into a host strain such as E. coli for expression, but other host species can be used with suitable expression vectors and possible codon optimization for that host species.

Expression of the desired enzymes from the constructed strain can be conducted in liquid culture, e.g., shaking flasks, bioreactors, chemostats, fermentation tanks and the like. Gene expression is typically induced by the addition of a suitable inducer, when the culture reaches an optical density of approximately 0.5-0.8. Induced cells can be grown for about 4-8 hours, at which point the cells can be pelleted and saved to −20° C. Expression of the desired protein can be confirmed by running cell pellet samples on SDS-PAGE.

The expressed enzyme can be directly assayed in crude cell lysates, simply by breaking the cells by chemical, enzymatic, heat or mechanical means. Depending on the expression level and activity of the enzyme, however, purification may be required to be able to measure enzyme activity over background levels. Purified enzymes can also allow for the in vitro assembly of the pathway, allowing for its controlled characterization. N-terminal or C-terminal HIS-tagged proteins can be purified using e.g., a Ni-NTA Spin Kit (Qiagen, Venlo, Limburg) following the manufacturer's protocol, or other methods could be used. The HIS-tag system was chosen for convenience only, and other tags are available for purification uses. Further, the proteins in the final assembled pathway need not be tagged if they are for in vivo use. Tagging was convenient, however, for the enzyme characterization work performed herein.

The reaction conditions for enzyme assays can vary greatly with the type of enzyme to be tested. In general, however, enzyme assays follow a similar general protocol. Purified enzyme or crude lysate is added to suitable reaction buffer. Reaction buffers typically contain salts, necessary enzyme cofactors, and are at the proper pH. Buffer compositions often change depending on the enzyme or reaction type. The reaction is initiated by the addition of substrate, and some aspect of the reaction related either to the consumption of a substrate or the production of a product is monitored.

Choice of the appropriate monitoring method depends on the compound to be measured. Spectrophotometric assays are convenient because they allow for the real time determination of enzyme activity by measuring the concentration dependent absorbance of a compound at a certain wavelength. There are not always compounds with a measurable absorbance at convenient wavelengths in the reaction, unfortunately. In these situations, other methods of chemical analysis may be necessary to determine the concentration of the involved compounds.

Gas chromatography (GC) is convenient for the quantification of volatile substances, of which fatty acids and aldehydes are of particular relevance. Internal standards, typically one or more molecules of similar type not involved in the reaction, is added to the reaction mixture, and the reaction mixture is extracted with an organic solvent, such as hexane. Fatty acid samples, for example, can be dried under a stream of nitrogen and converted to their trimethylsilyl derivatives using BSTFA and pyridine in a 1:1 ratio. After 30 minutes of incubation, the samples are once again dried and resuspended in hexane to be applied to the GC. Samples can be run e.g., on an Agilent 7890B Series Custom Gas Chromatography system equipped with a 5977B Inert Plus Mass Selective Detector Turbo EI Bundle and an Agilent HP-5-ms capillary column (Agilent Technologies, CA).

Strain construction for the in vivo pathway operation will allow for the well-defined, controlled expression of the enzymes of the pathway. As before, E. coli or yeast will be a host of choice for the in vivo pathway, but other hosts could be used. The Duet system (Novagen, Darmstadt, Germany), allows for the simultaneous expression of up to eight proteins by induction with IPTG in E. coli, and initial experiments used this host.

Pathway enzymes can also be inserted into the host chromosome, allowing for the maintenance of the pathway without requiring antibiotics to ensure the continued upkeep of plasmids. There are also, theoretically, an infinite number of genes that can be placed on the chromosome, as chromosomal expression does not require separate origins of replication as is the case with plasmid expression.

DNA constructs for chromosomal integration usually include an antibiotic resistance marker with flanking FRT sites for removal, a well characterized promoter, a ribosome binding site, the gene of interest, and a transcriptional terminator. The overall product is a linear DNA fragment with 50 base pairs of homology for the target site on the chromosome flanking each side of the construct.

However, the Flp-FRT recombination method is only one example of adding genes to a chromosome, and other systems are available, such as the RecBCD pathway, the RecF pathway, RecA recombinase, non-homologous end joining (NHEJ), Cre-Lox recombination, TYR recombinases and integrases, SER resolvases/invertases, SER integrases, PhiC31 Integrase, and the like. Chromosomal modifications in E. coli can also achieved by the method of recombineering, as known to those skilled in the art.

In a recombineering method, for example, the cells are prepared for electroporation following standard techniques, and the cells transformed with linear DNA that contains flanking 50 base pair targeting homology for the desired modification site. For seamless integration of a DNA construct, a two-step approach can be taken using a cassette that contains both positive and negative selection markers, such as the combination of cat and sacB. In the first round of recombineering, the cat-sacB cassette with targeting homology for the desired modification site is introduced to the cells. The cat gene provides resistance to chloramphenicol, which allows for positive recombinants to be selected for on solid media containing chloramphenicol. A positive isolate can be subjected to a second round of recombineering introducing the desired DNA construct with targeting homology for sites that correspond to the removal of the cat-sacB cassette. The sacB gene encodes for an enzyme that provides sensitivity to sucrose. Thus, growth on media containing sucrose allows for the selection of recombinants in which the cat-sacB construct was removed. P1 phage lysates can be made from isolates confirmed by PCR and sequencing. The lysates can be used to transduce the modification into desired strains, as described previously.

Engineered strains expressing the designed pathway can be cultured under the following or similar conditions. Overnight cultures started from a single colony can be used to inoculate flasks containing appropriate media. Cultures are grown for a set period of time, and the culture media analyzed. The conditions will be highly dependent on the specifications of the actual pathway and what exactly is to be tested. For example, the ability for the pathway to be used for autotrophic growth can be tested by the use of formate or formaldehyde as a substrate in MOPS minimal media, as described by Neidhardt et al., supplemented with appropriate antibiotics, and inducers. Mixotrophic growth can be characterized by the addition of both single carbon compounds and glucose or glycerol.

Analysis of culture media after fermentation provides insight into the performance of the engineered pathway. Quantification of longer chain fatty acid products can be analyzed by GC. Other metabolites, such as short chain organic acids and substrates such as glucose or glycerol can be analyzed by HPLC.

Following the construction of a suitable strain containing the engineered pathway, fermentations of the developed strains can be performed to evaluate the effectiveness of the pathway at its intended goal, the production of products from single carbon compounds. The organism can be evaluated for growth on a variety of single carbon substrates, from methane to $CO_2$ and $H_2$, either autotrophically or mixotrophically, with the inclusion of an additional carbon source. The products produced by the organism can be measured by HPLC or GC, and indicators of performance such as growth rate, productivity, titer, yield, or carbon efficiency can be determined.

Further evaluation of the interaction of the heterologously expressed pathway enzymes with each other and with the host system can allow for the optimization of pathway performance and minimization deleterious effects. Because the pathway is under synthetic control, rather than under the organism's natively evolved regulatory mechanisms, the expression of the pathway can be tuned to avoid potential issues that slow cell growth or production and to optimize production of desired compounds.

For example, one potential issue might be the excessive overexpression of protein, which could lead to depletion of resources for cellular growth and product formation or induce a stress response in the host organism. Additionally, an imbalance in relative enzyme activities might restrict overall carbon flux throughout the pathway, leading to suboptimal production rates and the buildup of pathway intermediates, which can inhibit pathway enzymes or be cytotoxic. Analysis of the cell cultures by HPLC or GC can reveal the metabolic intermediates produced by the constructed strains. This information can point to potential pathway issues. Additionally, -omics techniques, such as microarray or 2D-PAGE can give information about gene expression or protein expression, respectively. Genome scale modeling allows for the identification of additional modifications to the host strain that might lead to improved performance. Deletion of competing pathways, for example, might increase carbon flux through the engineered pathway for product production.

As an alternative to the in vivo expression of the pathway, a cell free, in vitro, version of the pathway can be constructed. By purifying the relevant enzyme for each reaction step, the overall pathway can be assembled by combining the necessary enzymes. With the addition of the relevant cofactors and single carbon compounds, the pathway can be assessed for its performance independently of a host.

The following description of examples provides additional details, any one of which can be subject to patenting in combination with any other. The specification in its entirety is to be treated as providing a variety of details that can be used interchangeably with other details, and it would be of inordinate length if one were to list every possible combination of genes/vectors/enzymes/hosts.

The invention is illustrated by the following non-limiting examples.

EXAMPLES

Example 1: Characterization Enzymes Catalyzing TPP-Dependent Acyloin Condensation Reactions Between a Ketone and Formyl-CoA The purpose of this example is to demonstrate that enzymes catalyzing TPP-dependent acyloin condensation reactions, such as 2-hydroxyacyl-CoA lyases, can facilitate the condensation between a ketone and formyl-CoA resulting in a 2-alkyl-2-hydroxyacyl-CoA molecule one carbon longer than the original carbonyl-containing compound.

Expression of the HACL from Rhodospirillales bacterium URHD0017 (RuHACL) was achieved using plasmid-based gene expression by cloning the desired gene into pCDF-Duet-1 (Novagen, Darmstadt, Germany) digested with appropriate restriction enzymes and by utilizing In-Fusion cloning technology (Clontech Laboratories, Inc., Mountain View, CA). Linear DNA fragments for insertion were created by gene synthesis of the codon optimized gene. Genes were synthesized by GeneArt (Life Technologies, Carlsbad, CA). Resulting In-Fusion reaction products were used to transform E. coli Stellar cells (Clontech Laboratories, Inc., Mountain View, CA), and clones identified by PCR screening were further confirmed by DNA sequencing.

Overnight cultures of the expression strains were grown in LB, which was used to inoculate 25 mL TB medium in a 250 mL baffled flask at 1%. The culture was grown at 30° C. and 250 rpm in an orbital shaker until OD550 reached 0.4-0.6, at which point expression was induced with 0.1 mM IPTG. 24 hours post inoculation, cells were harvested by centrifugation. The cell pellets were washed once with cold 9 g/L NaCl solution and stored at −80° C. until needed. Antibiotics were included where appropriate at the following concentrations: ampicillin (100 µg/mL), carbenicillin (50 µg/mL), kanamycin (50 µg/mL), spectinomycin (50 µg/mL), and chloramphenicol (34 µg/mL).

Cell extracts were prepared by resuspending the frozen cell pellets in cold 50 mM KPi pH 7.4 to an approximate OD550 of 40. The cells were disrupted by sonication on ice using a Branson Sonifier 250 (5 minutes with a 25% duty cycle and output control set at 3). The mixture was centrifuged (17000×g, 4° C., 15 min), and the supernatant was concentrated by application to a 10,000 MWCO Amicon ultrafiltration centrifugal device (Millipore, Billerica, MA). Protein concentration was estimated by the Bradford method, and the cell extract protein concentrations were normalized to approximately 35 g/L. 50 µL aliquots of the cell extracts were prepared in PCR tubes and frozen at −80° C. until needed.

Frozen cell pellets were resuspended in cold lysis buffer (50 mM NaPi pH 7.4, 300 mM NaCl, 10 mM imidazole, 0.1% Triton-X 100) to an approximate OD550 of 40, to which 1 mg/mL of lysozyme and 250 U of Benzonase nuclease was added. The mixture was further treated by sonication on ice using a Branson Sonifier 250 (5 minutes with a 25% duty cycle and output control set at 3), and centrifuged at 7500×g for 15 minutes at 4° C. The supernatant was applied to a chromatography column containing 1 mL TALON metal affinity resin (Clontech Laboratories, Inc., Mountain View, CA), which had been pre-equilibrated with the lysis buffer. The column was then washed first with 10 mL of the lysis buffer and then twice with 20 mL of wash buffer (50 mM NaPi pH 7.4, 300 mM NaCl, 20 mM imidazole). The his-tagged protein of interest was eluted with 1-2 applications of 4 mL elution buffer (50 mM NaPi pH 7.4, 300 mM NaCl, 250 mM imidazole). The eluate was collected and applied to a 10,000 MWCO Amicon ultrafiltration centrifugal device (Millipore, Billerica, MA), and the concentrate (~100 µL) was washed twice with 4 mL of 50 mM KPi pH 7.4 for desalting. Protein concentrations were estimated by the Bradford method. Purified protein was saved in 20 µL aliquots at −80° C. until needed.

SDS-PAGE was performed using NuPAGE 12% Bis-Tris Protein Gels with MOPS running buffer and stained with SimplyBlue SafeStain according to manufacturer protocols (ThermoFisher Scientific, Waltham, MA).

Figure 6:
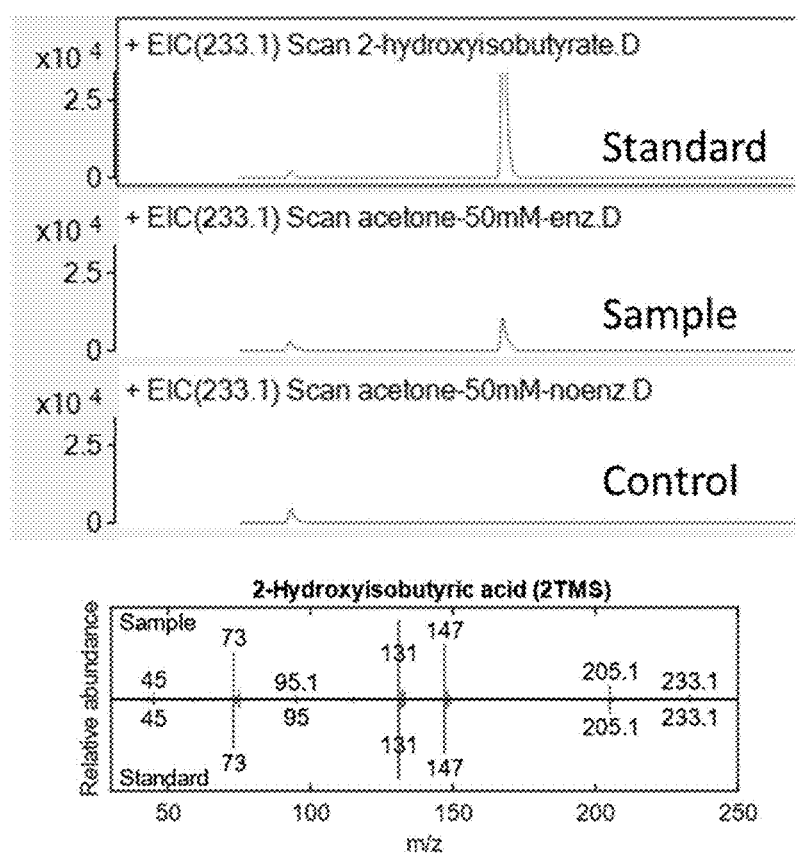
FIG. 6. Synthesis of a product derived from a substituted/functionalized 2-hydroxyacyl-CoA intermediate generated by an acyloin condensation reaction between formyl-CoA and a ketone. Production of 2-hydroxyisobutyric acid from acetone and formyl-CoA in a reaction mixture is shown. Top: Extracted ion chromatogram of a 2-hydroxyisobutyrate standard, the reaction sample, and a no enzyme control. Production of 2-hydroxyisobutyrate was observed in the sample, but not in the no enzyme control. Bottom: Head-to-tail mass spectra of a 2-hydroxybutyric acid standard and the reaction sample, confirming the identity of 2-hydroxyisobutyric acid produced in the reaction mixture.

Purified RuHACL was assayed in the synthetic direction by incubating the purified enzyme in a reaction containing 50 mM KPi pH 7.4, 2.5 mM $MgCl_2$, 0.1 mM TPP, 1.5 mM formyl-CoA, 50 mM acetone, and 1 µM HACL for 18 hours at room temperature on a Labquake rotisserie shaker. The acyl-CoA products were converted to their carboxylic acid form by base hydrolysis. To a 160 µL sample, 40 µL of 0.5 M NaOH was added, to which an additional 50 µL of ammonium sulfate solution acidified with 1% sulfuric acid was added. Following this analysis, 2-hydroxyisobutyric acid, the acid product resulting from hydrolysis of 2-hydroxyisobutyryl-CoA formed via condensation of acetone with formyl-CoA acid, was detected in the reaction mixture (FIG. 6).

These results demonstrate that enzymes catalyzing TPP-dependent acyloin condensation reactions, such as HACLs, can catalyze a previously unknown C1 condensation/chain elongation reaction between formyl-CoA and a ketone.

Example 2: Characterization Enzymes Catalyzing TPP-Dependent Acyloin Condensation Reactions Between a Functionalized Aldehyde and Formyl-CoA The purpose of this example is to demonstrate that enzymes catalyzing TPP-dependent acyloin condensation reactions, such as 2-hydroxyacyl-CoA lyases, can facilitate the condensation between a functionalized aldehyde and formyl-CoA resulting in a functionalized 2-hydroxyacyl-CoA molecule one carbon longer than the original carbonyl-containing compound.

Expression of the HACL from Rhodospirillales bacterium URHD0017 (RuHACL) was achieved using plasmid-based gene expression by cloning the desired gene into pCDF-Duet-1 (Novagen, Darmstadt, Germany) digested with appropriate restriction enzymes and by utilizing In-Fusion cloning technology (Clontech Laboratories, Inc., Mountain View, CA). Linear DNA fragments for insertion were created by gene synthesis of the codon optimized gene. Genes were synthesized by GeneArt (Life Technologies, Carlsbad, CA). Resulting In-Fusion reaction products were used to transform E. coli Stellar cells (Clontech Laboratories, Inc., Mountain View, CA), and clones identified by PCR screening were further confirmed by DNA sequencing.

Overnight cultures of the expression strains were grown in LB, which was used to inoculate 25 mL TB medium in a 250 mL baffled flask at 1%. The culture was grown at 30° C. and 250 rpm in an orbital shaker until OD550 reached 0.4-0.6, at which point expression was induced with 0.1 mM IPTG. 24 hours post inoculation, cells were harvested by centrifugation. The cell pellets were washed once with cold 9 g/L NaCl solution and stored at −80° C. until needed. Antibiotics were included where appropriate at the following concentrations: ampicillin (100 µg/mL), carbenicillin (50 µg/mL), kanamycin (50 µg/mL), spectinomycin (50 µg/mL), and chloramphenicol (34 µg/mL).

Cell extracts were prepared by resuspending the frozen cell pellets in cold 50 mM KPi pH 7.4 to an approximate OD550 of 40. The cells were disrupted by sonication on ice using a Branson Sonifier 250 (5 minutes with a 25% duty cycle and output control set at 3). The mixture was centrifuged (17000×g, 4° C., 15 min), and the supernatant was concentrated by application to a 10,000 MWCO Amicon ultrafiltration centrifugal device (Millipore, Billerica, MA). Protein concentration was estimated by the Bradford method, and the cell extract protein concentrations were normalized to approximately 35 g/L. 50 µL aliquots of the cell extracts were prepared in PCR tubes and frozen at −80° C. until needed.

Frozen cell pellets were resuspended in cold lysis buffer (50 mM NaPi pH 7.4, 300 mM NaCl, 10 mM imidazole, 0.1% Triton-X 100) to an approximate OD550 of 40, to which 1 mg/mL of lysozyme and 250 U of Benzonase nuclease was added. The mixture was further treated by sonication on ice using a Branson Sonifier 250 (5 minutes with a 25% duty cycle and output control set at 3), and centrifuged at 7500×g for 15 minutes at 4° C. The supernatant was applied to a chromatography column containing 1 mL TALON metal affinity resin (Clontech Laboratories, Inc., Mountain View, CA), which had been pre-equilibrated with the lysis buffer. The column was then washed first with 10 mL of the lysis buffer and then twice with 20 mL of wash buffer (50 mM NaPi pH 7.4, 300 mM NaCl, 20 mM imidazole). The his-tagged protein of interest was eluted with 1-2 applications of 4 mL elution buffer (50 mM NaPi pH 7.4, 300 mM NaCl, 250 mM imidazole). The eluate was collected and applied to a 10,000 MWCO Amicon ultrafiltration centrifugal device (Millipore, Billerica, MA), and the concentrate (~100 µL) was washed twice with 4 mL of 50 mM KPi pH 7.4 for desalting. Protein concentrations were estimated by the Bradford method. Purified protein was saved in 20 µL aliquots at −80° C. until needed.

SDS-PAGE was performed using NuPAGE 12% Bis-Tris Protein Gels with MOPS running buffer and stained with SimplyBlue SafeStain according to manufacturer protocols (ThermoFisher Scientific, Waltham, MA).

Figure 7:
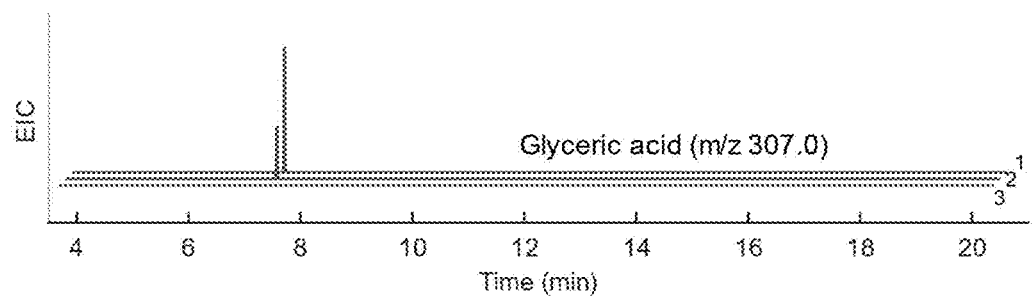
FIG. 7. Synthesis of a product derived from a substituted/functionalized 2-hydroxyacyl-CoA intermediate generated by an acyloin condensation reaction between formyl-CoA and a functionalized aldehyde. Production of glyceric acid from glycolaldeyhde and formyl-CoA in a reaction mixture is shown. Line 1 corresponds to a standard of the indicated compound. Line 2 corresponds to a sample containing RuHACL in which the indicated compound is observed. Line 3 corresponds to a control sample containing no enzyme in which no product is detected.

Purified RuHACL was assayed in the synthetic direction by incubating the purified enzyme in a reaction containing 50 mM KPi pH 7.4, 2.5 mM MgCl$_2$, 0.1 mM TPP, 1.5 mM formyl-CoA, 50 mM glycolaldehyde, and 1 µM HACL for 18 hours at room temperature on a Labquake rotisserie shaker. The acyl-CoA products were converted to their carboxylic acid form by base hydrolysis. To a 160 µL sample, 40 µL of 0.5 M NaOH was added, to which an additional 50 µL of ammonium sulfate solution acidified with 1% sulfuric acid was added. Following this analysis, glyceric acid, the acid product resulting from hydrolysis of glyceryl-CoA formed via condensation of glycolaldehyde with formyl-CoA acid, was detected in the reaction mixture (FIG. 7).

These results demonstrate that enzymes catalyzing TPP-dependent acyloin condensation reactions, such as HACLs, can catalyze a previously unknown C1 condensation/chain elongation reaction between formyl-CoA and functionalized aldehydes.

Example 3: One-Carbon Elongation of Functionalized Aldehydes and Ketones In Vivo The purpose of this example is to demonstrate the aspect of the invention pertaining to one-carbon elongation of functionalized aldehydes or ketones by formyl-CoA for product synthesis in vivo.

Figure 8:
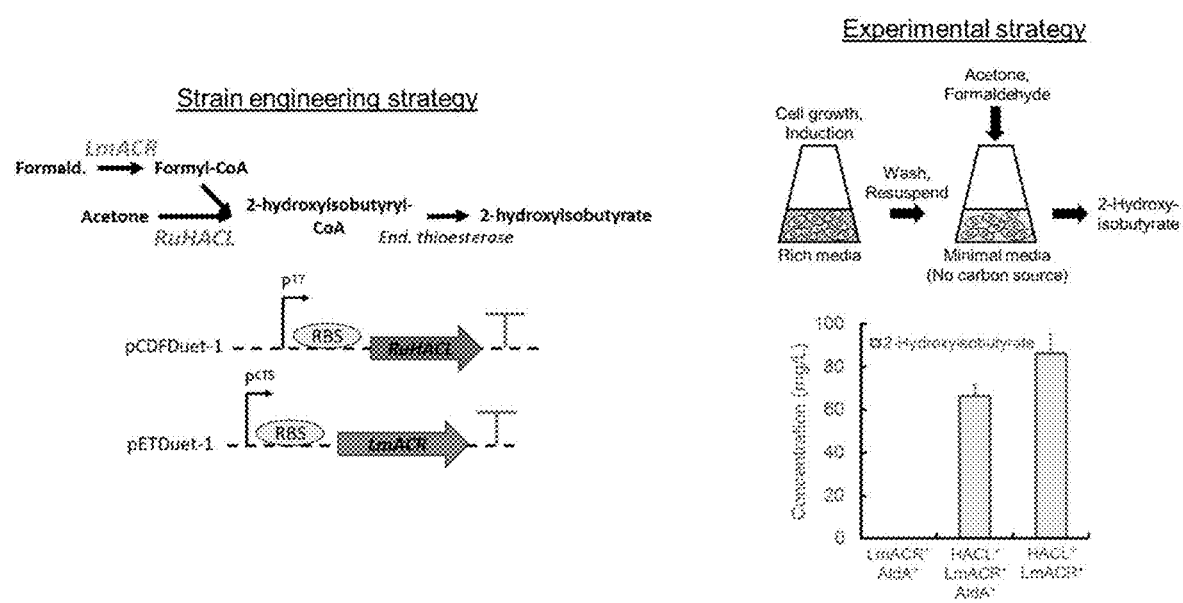
FIG. 8. in vivo synthesis of a product derived from a substituted/functionalized 2-hydroxyacyl-CoA intermediate generated by an acyloin condensation reaction between formyl-CoA and a ketone. Production of 2-hydroxyisobutyrate from acetone and formaldehyde using engineered recombinant microorganisms. Left: The overall strategy involved in engineering the microorganism requires expression of two enzymes. LmACR converts formaldehyde to formyl-CoA, while HACL condenses acetone and formyl-CoA to 2-hydroxyisobutyryl-CoA. Thioesterases endogenous to the organism convert 2-hydroxyisobutyryl-CoA to 2-hydroxyisobutyrate. Right: The product synthesis strategy involves resuspending cells expressing the required enzymes in a media with acetone and formaldehyde provided. 2-hydroxyisobutyrate was produced at around 90 mg/L.

To implement the above C1 elongation pathway for 2-hydroxyisobutyrate production in vivo, we engineered vectors to independently control expression of HACL from Rhodospirillales bacterium URHD0017 (RuHACL) and the acyl-CoA reductase from *Listeria monocytogenes* (LmACR), with RuHACL under control of the IPTG-inducible T7 promoter in pETDuet-1 and LmACR under control of a cumate-inducible T5 promoter in pCDFDuet-1 (FIG. 8). As a host for these vectors, we used an engineered strain of *E. coli* based on MG1655(DE3) with knockouts for formaldehyde (ΔfrmA) and formate (ΔfdhF ΔfdnG ΔfdoG) oxidation as well as for glycolate utilization (ΔglcD), which we expected could compete or interfere with the analysis of our pathway (FIG. 8).

In vivo product synthesis was conducted using the minimal medium designed by Neidhardt et al., modified to contain 125 mM MOPS and supplemented with indicated amounts of carbon source(s), 1.48 mM K$_2$HPO$_4$, 5 mM (NH$_4$)$_2$SO$_4$, 30 mM NH$_4$Cl, 2 mM MgSO$_4$, and 15 µM thiamine-HCl unless otherwise stated. Cells were initially grown in 125 mL baffled flasks (Wheaton, Millville, NJ) containing 25 mL of the above media further supplemented with 20 g/L glycerol, 10 g/L tryptone, and 5 g/L yeast extract. A single colony of the desired strain was cultivated overnight (14-16 hrs) in LB medium with appropriate antibiotics and used as the inoculum (1%). Antibiotics (50 µg/mL carbenicillin, 50 µg/mL spectinomycin) were included when appropriate. Cultures were then incubated at 30° C. and 250 rpm in a Lab Companion SI-600 rotary shaker (Jeio Tech, Seoul, South Korea) until an OD550 of ~0.4 was reached, at which point appropriate amounts of inducer(s) (isopropyl β-D-1-thiogalactopyranoside and cumate) were added. Flasks were incubated for a total of 24 hrs post-inoculation.

Cells from the above pre-cultures were then centrifuged (5000×g, 22° C.), washed twice with the above minimal media without any carbon source, and resuspended to an optical density ~10 (FIG. 8). 5 mL of this cell suspension and indicated amounts of carbon source (e.g. formaldehyde) was added to 25 mL Pyrex Erlenmeyer flasks (Corning Inc., Corning, NY) and sealed with foam plugs filling the necks. 25 mM acetone and 5 mM formaldehyde were added at 0 hr, with additional 5 mM formaldehyde added at 1, 2, and 3 hrs Flasks were incubated at 30° C. and 200 rpm in an NBS I24 Benchtop Incubator Shaker (New Brunswick Scientific Co., Inc., Edison, NJ). After incubation at 30° C. for 24 hours, the cells were pelleted by centrifugation and the media analyzed. The expected product 2-hydroxyisobutyric acid was detected in the media, indicating production by the engineered organism (FIG. 8).

Example 4: Aldose Elongation for Iterative Carbon Chain Elongation

Figure 9:
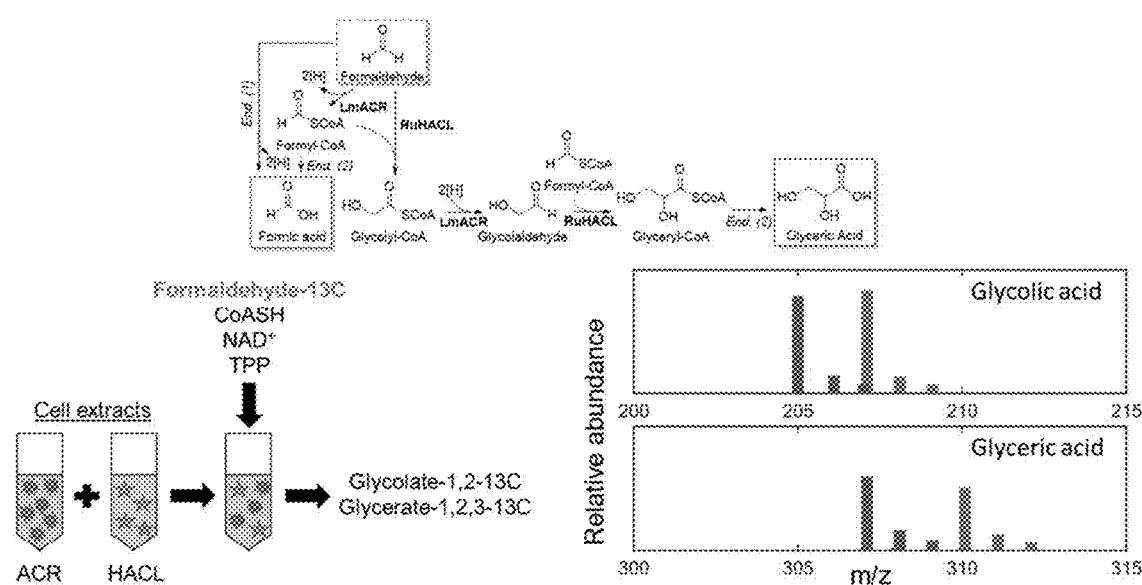
FIG. 9. Iterative elongation of a carbon backbone or aldose elongation involving the generation of a functionalized aldehyde from a C1 substrate and subsequent multicarbon product synthesis via the substituted/functionalized 2-hydroxyacyl-CoA intermediate generated by an acyloin condensation reaction between formyl-CoA and the functionalized aldehyde. Top: Schematic of the operation of aldose elongation by iterative action of LmACR and RuHACL. LmACR converts formaldehyde to formyl-CoA, which is condensed with formaldehyde by RuHACL. The resulting glycolyl-CoA is reduced to glycolaldehyde (functionalized aldehyde) by LmACR and further condensed with formyl-CoA by RuHACL. Glyceryl-CoA is hydrolyzed by endogenous thioesterases to glyceric acid. Bottom, left: Overall strategy involved incubating formaldehyde and cofactors with extracts of *E. coli* expressing ACR and HACL. Bottom, right: Mass spectra of glycolic acid and glyceric acid standards (blue) and reaction samples (orange). The use of isotope-labeled formaldehyde demonstrated that the detected glycolic acid and glyceric acid were derived from formaldehyde as demonstrated by the +2 and +3 m/z shifts, respectively.

The purpose of this example is to demonstrate the aspect of the invention pertaining to the iterative elongation of a carbon backbone by one carbon units, known as aldose elongation. Cell extracts of *E. coli* expressing the enzymes LmACR and RuHACL were prepared as described above. In a reaction mixture, these cell extracts were combined with 50 mM formaldehyde-13C, 4 mM $MgCl_2$, 0.1 mM TPP, 2.5 mM CoASH, and 5 mM $NAD^+$ in an aqueous buffer comprising 50 mM potassium phosphate pH 7.4. After incubation at room temperature for one hour, the reaction products were analyzed by GC-MS. Detection of glyceric acid-1,2,3-13C indicated the production of a three-carbon product from the one-carbon substrate formaldehyde-13C by the iterative function of ACR and HACL (FIG. 9).

Example 5: Identification of Prokaryotic 2-Hydroxyacyl-CoA Lyases

The purpose of this example is to demonstrate the identification of enzymes, such as 2-hydroxyacyl-CoA lyases, that can catalyze the TPP-dependent acyloin condensation between an aldehyde or ketone with formyl-CoA resulting in a molecule one carbon longer than the original carbonyl-containing compound. We have previously cloned and expressed in *E. coli* a codon optimized version of the 2-hydroxyacyl-CoA lyase HACL1 from *Homo sapiens* (HsHACL1) and demonstrated its ability to condense various chain length aldehydes with formyl-CoA (see, for example, in WO2016/069929A1 and U.S. Pat. App. Pub. No. US20190100741A1). While we were able to utilize this eukaryotic enzyme in a bacterial system, in many cases low functional expression of eukaryotic enzyme in bacterial systems limits their overall functionality in the context of an in vivo pathway.

Figure 10:
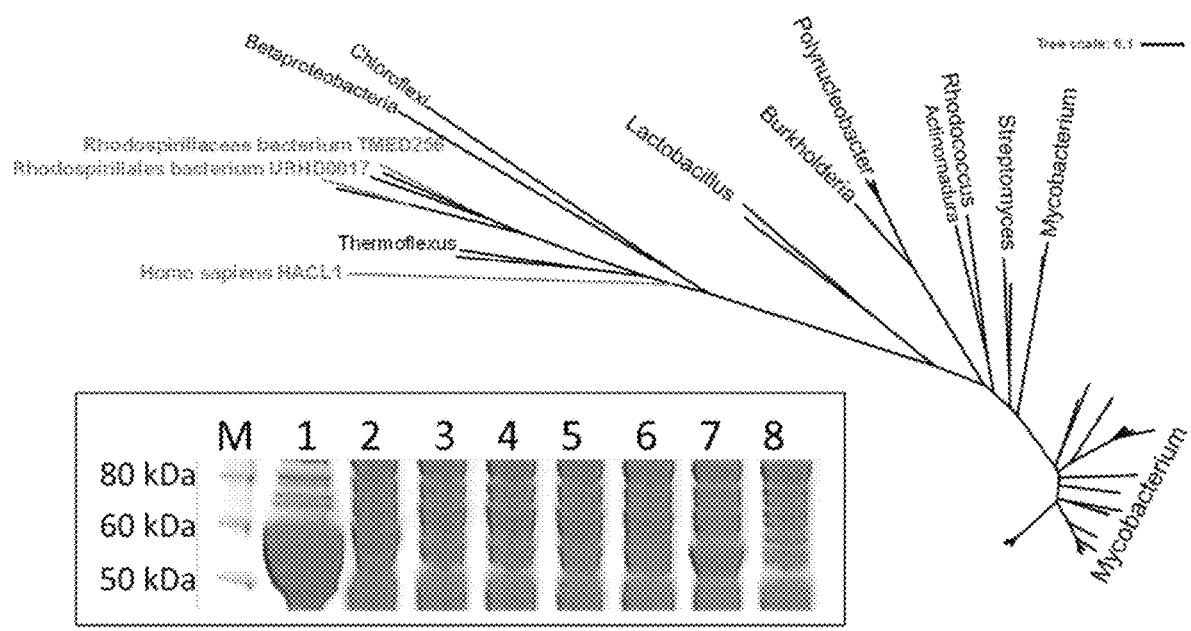
FIG. 10. Identification prokaryotic HACLs. The tree of the results of a BLASTp analysis performed using *Homo sapiens* HACL1 (HsHACL1) as the query sequence with eukaryotic organisms excluded reveals a group of enzymes from organisms from the classes Chloroflexia, Alphaproteobacteria, Betaproteobacteria, and Thermoflexia that appear to have higher similarity to the human enzyme than the other hits, the majority of which originate from *Mycobacterium*. Inset: SDS-PAGE of HACL and Oxc expression in *E. coli* BL21(DE3) cell extract. M: Marker; 1: EcOxc; 2: OfOxc; 3: CbHACL; 4: RtHACL; 5: HsHACL2; 6: HsHACL1; 7: RuHACL; 8: BL21(DE3) extract. Expected HACL sizes are typically between 50-60 kDa.

We thus sought to identify variants of HACL native to prokaryotes, with the expectation of improved soluble expression. While α-oxidation has been hypothesized to take place in prokaryotes, the existence of prokaryotic HACLs has never been confirmed. Protein BLAST limited to prokaryotes returned hits that were nearly all annotated as oxalyl-CoA decarboxylase (Oxc), a related TPP-dependent enzyme that also catalyzes degradative reactions involving formyl-CoA (FIG. 10). This analysis further revealed a group of enzymes from organisms from the classes Chloroflexia, Alphaproteobacteria, Betaproteobacteria, and Thermoflexia that appear to have higher similarity to the human enzyme than the other hits, the majority of which originate from *Mycobacterium*. We selected variants based on similarity to HsHACL1 that were primarily from mesophiles, and synthesized, cloned, and expressed their codon-optimized genes.

Expression of selected enzyme variants was achieved using plasmid-based gene expression by cloning the desired gene(s) into pETDuet-1 or pCDFDuet-1 (Novagen, Darmstadt, Germany) digested with appropriate restriction enzymes and by utilizing In-Fusion cloning technology (Clontech Laboratories, Inc., Mountain View, CA). Linear DNA fragments for insertion were created via PCR of the open reading frame of interest (for genes native to *E. coli*) or by gene synthesis of the codon optimized gene. Genes were synthesized by GeneArt (Life Technologies, Carlsbad, CA). Resulting In-Fusion reaction products were used to transform *E. coli* Stellar cells (Clontech Laboratories, Inc., Mountain View, CA), and clones identified by PCR screening were further confirmed by DNA sequencing.

Overnight cultures of the expression strains were grown in LB, which was used to inoculate 25 mL TB medium in a 250 mL baffled flask at 1%. The culture was grown at 30° C. and 250 rpm in an orbital shaker until OD550 reached 0.4-0.6, at which point expression was induced with 0.1 mM IPTG. 24 hours post inoculation, cells were harvested by centrifugation. The cell pellets were washed once with cold 9 g/L NaCl solution and stored at −80° C. until needed.

Antibiotics were included where appropriate at the following concentrations: ampicillin (100 μg/mL), carbenicillin (50 μg/mL), kanamycin (50 μg/mL), spectinomycin (50 μg/mL), and chloramphenicol (34 μg/mL).

Cell extracts were prepared by resuspending the frozen cell pellets in cold 50 mM KPi pH 7.4 to an approximate OD550 of 40. The cells were disrupted by sonication on ice using a Branson Sonifier 250 (5 minutes with a 25% duty cycle and output control set at 3). The mixture was centrifuged (17000×g, 4° C., 15 min), and the supernatant was concentrated by application to a 10,000 MWCO Amicon ultrafiltration centrifugal device (Millipore, Billerica, MA). Protein concentration was estimated by the Bradford method, and the cell extract protein concentrations were normalized to approximately 35 g/L. 50 μL aliquots of the cell extracts were prepared in PCR tubes and frozen at −80° C. until needed.

SDS-PAGE was performed using NuPAGE 12% Bis-Tris Protein Gels with MOPS running buffer and stained with SimplyBlue SafeStain according to manufacturer protocols (ThermoFisher Scientific, Waltham, MA).

Of the various enzymes selected for cloning and expression analysis, which included *Escherichia coli* Oxc, *Oxalobacter formigenes* Oxc, Chloroflexi bacterium SCGC AB-629-P13 HACL, Rhodospirillales bacterium TMED256 HACL, *Homo sapiens* HACL2, *Homo sapiens* HACL1, and Rhodospirillales bacterium URHD0017 HACL, one variant, from R. bacterium URHD0017 (RuHACL), had higher soluble expression than the others (FIG. 10). This high soluble expression facilitated the direct purification of RuHACL from *E. coli* cell extract.

For protein purification, *E. coli* cell pellets expressing the desired his-tagged enzymes were prepared as described above. The frozen cell pellets were resuspended in cold lysis buffer (50 mM NaPi pH 7.4, 300 mM NaCl, 10 mM imidazole, 0.1% Triton-X 100) to an approximate OD550 of 40, to which 1 mg/mL of lysozyme and 250 U of Benzonase nuclease was added. The mixture was further treated by sonication on ice using a Branson Sonifier 250 (5 minutes with a 25% duty cycle and output control set at 3), and centrifuged at 7500×g for 15 minutes at 4° C. The supernatant was applied to a chromatography column containing 1 mL TALON metal affinity resin (Clontech Laboratories, Inc., Mountain View, CA), which had been pre-equilibrated with the lysis buffer. The column was then washed first with 10 mL of the lysis buffer and then twice with 20 mL of wash buffer (50 mM NaPi pH 7.4, 300 mM NaCl, 20 mM imidazole). The his-tagged protein of interest was eluted with 1-2 applications of 4 mL elution buffer (50 mM NaPi pH 7.4, 300 mM NaCl, 250 mM imidazole). The eluate was collected and applied to a 10,000 MWCO Amicon ultrafiltration centrifugal device (Millipore, Billerica, MA), and the concentrate (~100 μL) was washed twice with 4 mL of 50 mM KPi pH 7.4 for desalting. Protein concentrations were estimated by the Bradford method. Purified protein was saved in 20 μL aliquots at −80° C. until needed.

Figure 11:
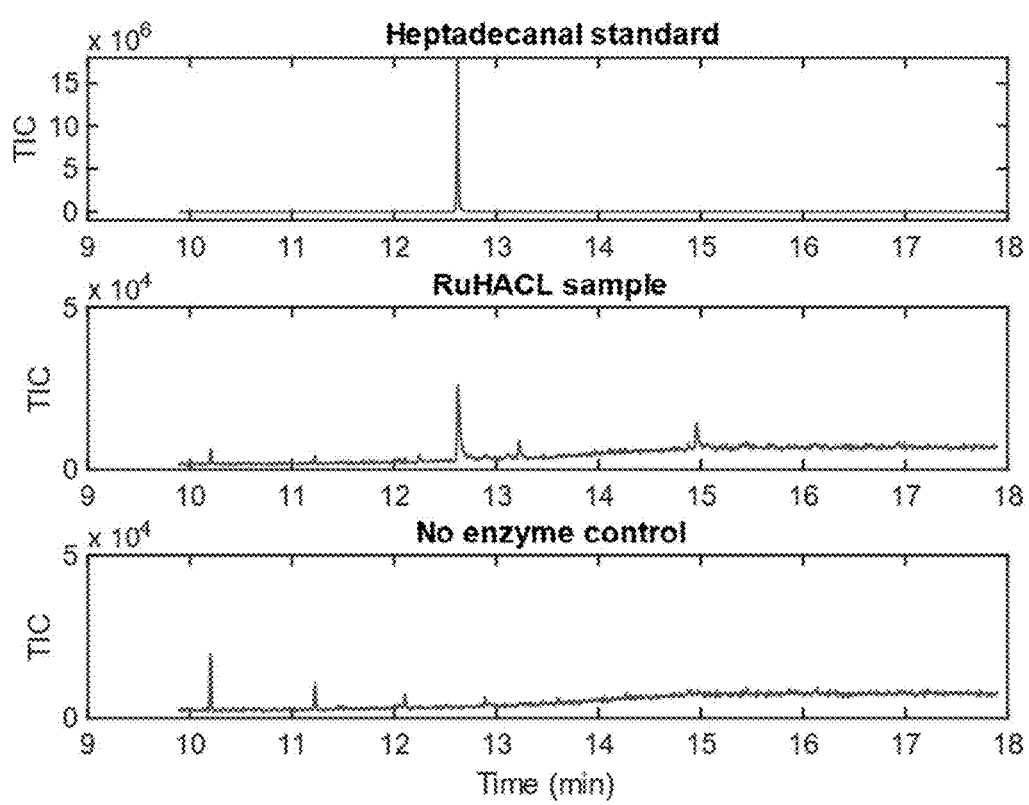
FIG. 11. Assay of Rhodospirillales bacterium URHD0017 HACL (RuHACL). RuHACL was assayed in the physiological direction by incubation with 2-hydroxyoctadecanoyl-CoA. After incubation, the expected product heptadecanal was observed in the sample containing RuHACL, indicating HACL activity.

When purified and assayed, RuHACL exhibited HACL activity, catalyzing the production of heptadecanal from 2-hydroxyoctadecanoyl-CoA (FIG. 11). Heptadecanal was analyzed by extraction of 500 μL samples twice with 500 μL of hexane. After evaporation to dryness, the residue was dissolved in 200 μL of hexane for GC analysis (1 μL injection with a 4:1 split ratio) using helium as the carrier gas at a flowrate of 1.5 mL/min and the following temperature profile: initial 50° C. (hold 3 min); ramp at 20° C./min to 270° C. (hold 6 min). The injector and detector temperature were 250° C. and 350° C., respectively.

Figure 12:
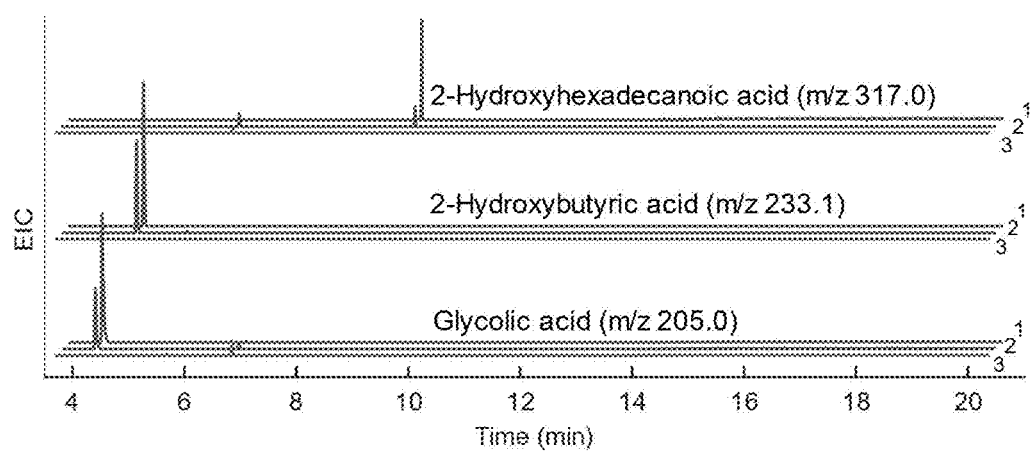
FIG. 12. Characterization of a prokaryotic HACL that catalyzes the condensation of formyl-CoA and various chain length aldehydes. Extracted ion chromatograms of Rhodospirillales bacterium URHD0017 HACL (RuHACL) enzyme assays analyzed by GC-MS reveal the production of 2-hydroxy products from formyl-CoA and nonanal, propionaldehyde, and formaldehyde. Line 1 corresponds to a standard of the indicated compound. Line 2 corresponds to a sample containing RuHACL in which the indicated compound is observed. Line 3 corresponds to a control sample containing no enzyme in which no product is detected.

Furthermore, RuHACL could catalyze the reverse reaction with a broad range of aldehyde substrates, ligating formyl-CoA with formaldehyde, propanal, and nonanal to produce glycolyl-CoA, 2-hydroxybutyryl-CoA, and 2-hydroxydecanoyl-CoA, respectively, as determined by the detection of their corresponding acid derivatives (FIG. 12). For this analysis, samples containing acyl-CoAs were first treated with 0.5 M NaOH to hydrolyze the thioesters and produce the carboxylic acid. Ammonium sulfate solution acidified with 1% sulfuric acid was then added to improve the efficiency of acid extraction. The resulting sample was extracted into 4 mL ethyl acetate by vigorous vortexing for 90 seconds. The organic phase was separated and evaporated to dryness under a stream of nitrogen. The residue was dissolved in 50 µL pyridine and 50 µL N,O-Bis(trimethylsilyl)trifluoroacetamide (BSTFA) and incubated at 60° C. for 15 minutes. Compound identification and analysis was performed by GC-MS using an Agilent 7890B Series Custom Gas Chromatography system equipped with a 5977B Inert Plus Mass Selective Detector Turbo EI Bundle (for identification) and an Agilent HP-5-ms capillary column (0.25 mm internal diameter, 0.25 µm film thickness, 30 m length). Samples were analyzed by GC (1 µL injection with a 4:1 split ratio) using helium as the carrier gas at a flowrate of 1.5 mL/min and the following temperature profile: initial 90° C. for 3 min; ramp at 15° C./min to 170° C.; ramp at 20° C./min to 300° C. and hold for 8 min. The injector and detector temperature were 250° C. and 350° C., respectively.

Example 6: Kinetics of RuHACL for the Ligation of Acetone with Formyl-CoA

The purpose of this example is to demonstrate the determination of the kinetic parameters of the enzyme catalyzed condensation reaction of acetone with formyl-CoA. 0.5 µM purified RuHACL was incubated with 1 mM formyl-CoA in a reaction mixture also containing 50 mM KPi pH 7.4, 2.5 mM $MgCl_2$, and 0.1 mM TPP. The concentration of acetone was varied, and room temperature reactions were carried out for 1 min. 40 µL samples were quenched by addition of 10 µL 0.5 M NaOH and placed on ice. 12.5 µL of a saturated ammonium sulfate solution acidified with 1% sulfuric acid was added and the samples were analyzed by HPLC for the determination of the initial reaction rates after centrifugation at 20817×g for 15 minutes. A curve of substrate vs. velocity was generated from this data and the data was fit to Michaelis-Menten parameters. The apparent $k_{cat}$ of RuHACL on acetone was 2.7±0.8 $s^{-1}$ while the KM was 1.57±0.68 M, corresponding to a catalytic efficiency of 1.7±0.9 $s^{-1}$ $M^{-1}$.

Figure 13:
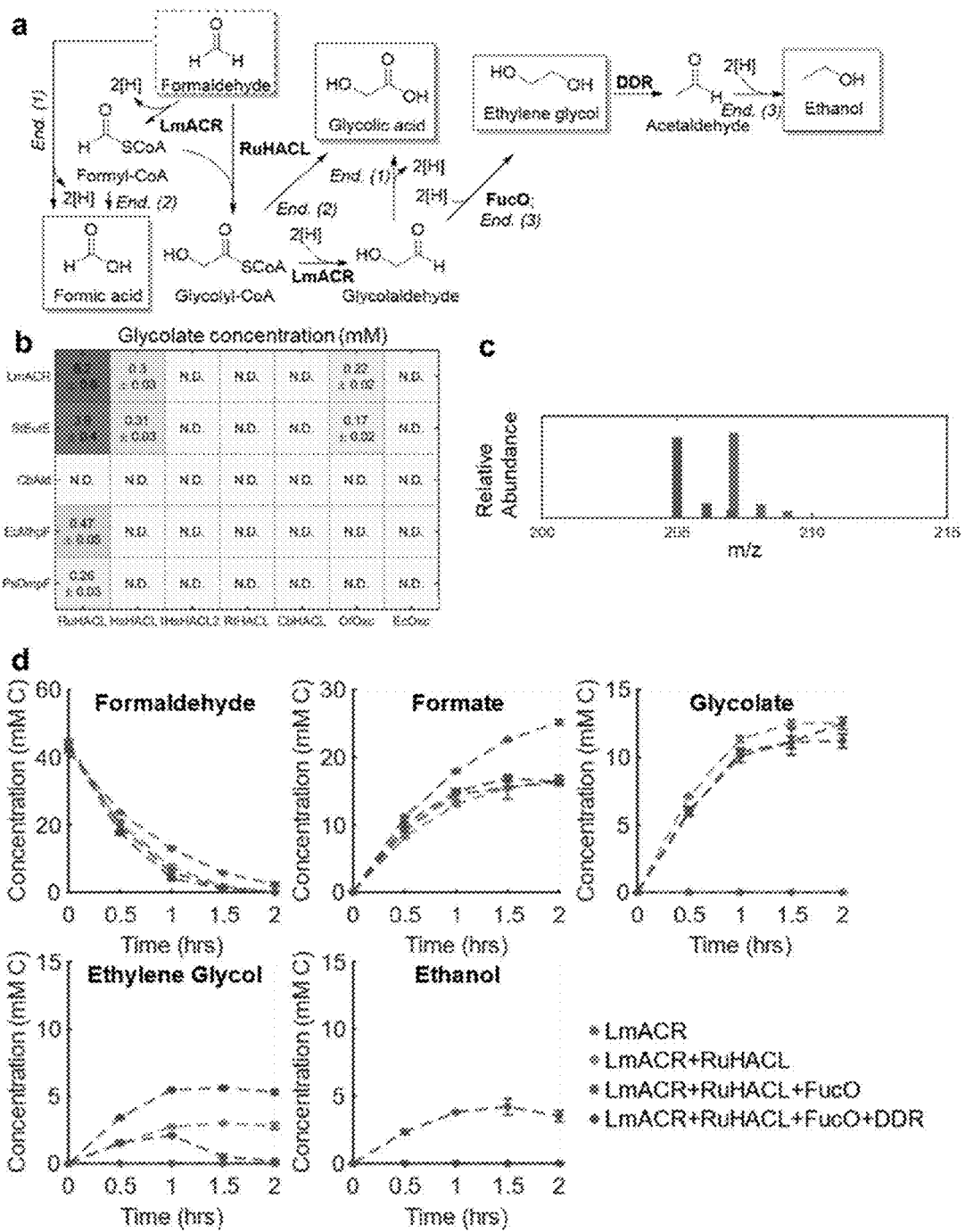
FIG. 13. Cell-free prototyping of a one carbon bioconversion pathway based on HACL. a, Overview of the reaction pathway for two carbon compound production based on the use of formaldehyde as the sole carbon substrate. Products that were detected in this work are boxed with a solid outline. Enzyme abbreviations: DDR: *Klebsiella oxytoca* diol dehydratase; End. (1): endogenous aldehyde dehydrogenase; End. (2): endogenous thioesterase; End. (3): endogenous alcohol dehydrogenase; FucO: *E. coli* 1,2-diol oxidoreductase; LmACR: *Listeria monocytogenes* acyl-CoA reductase; RuHACL: Rhodospirillales bacterium URHD0017 HACL. b, Production of glycolic acid in cell-free reactions mixing ACR and HACL variants. Values are expressed as mean±standard deviation, where standard deviation was determined for n=3 replicates of the LmACR+ RuHACL case and applied to other samples on a percentage basis. c, Mass spectra of the molecular ion of derivatized glycolic acid produced in the cell-free system when 13C-labeled formaldehyde was provided as the sole carbon substrate in comparison to unlabeled standards. d, Product and substrate profiles of cell-free systems with pathway enzymes. Concentrations are given on a carbon basis.

Example 7: Cell-Free Prototyping of One Carbon Bioconversion Pathway Based on Prokaryotic Enzymes Catalyzing TPP-Dependent Acyloin Condensation Reactions The purpose of this example is to demonstrate the cell-free method for prototyping the use of various enzymes catalyzing TPP-dependent acyloin condensation reactions, such 2-hydroxyacyl-CoA lyases, in the context of a bioconversion pathway for one-carbon substrate conversion. We prototyped the use of enzymes identified in the previous example as part of a synthetic pathway for the conversion of C1 substrates to multi-carbon products using formaldehyde as the sole carbon source (FIG. 13A). The most immediate two-carbon ligation product of the pathway is glycolic acid, which can be readily hydrolyzed from glycolyl-CoA by endogenously expressed thioesterases. Thus, the synthesis of glycolic acid from formaldehyde using HACL only requires the additional generation of formyl-CoA, which can be accomplished by the use of an acyl-CoA reductase (ACR).

Cell-free reactions for pathway prototyping contained 50 mM KPi pH 7.4, 4 mM $MgCl_2$, 0.1 mM TPP, 2.5 mM CoASH, 5 mM $NAD^+$, and 50 mM formaldehyde. For time course experiments, 0.1 mM coenzyme B12 was added. Individual cell extract loading was around 4.4 g/L protein (⅛ of the reaction volume), and the amount of protein added to each reaction was normalized with BL21(DE3) extract to ~26 g/L protein (¾ of the reaction volume). Reactions were incubated at room temperature for one hour unless otherwise specified. ¼ of the reaction volume of saturated ammonium sulfate solution acidified with 1% sulfuric acid was added to terminate the reactions. Samples were centrifuged at 20817×g for 15 minutes and the supernatant analyzed by HPLC or GC-MS as described below. For isotope labeling experiments, 13C formaldehyde (Cambridge Isotope Laboratories, Tewksbury, MA) was used.

We combined extracts of *E. coli*, prepared as described in the previous example(s), expressing variants of HACL and ACR to rapidly screen for the best performing combinations. As expected based on soluble expression, RuHACL was the best performing HACL variant, with HsHACL1 also enabling product synthesis (FIG. 13B). Interestingly, the variant of oxalyl-CoA decarboxylase from *Oxalobacter formigenes* (OfOxc) also appeared capable of catalyzing the pathway. Of the ACRs tested, the variant from *Listeria monocytogenes* (LmACR) was best suited for enabling the pathway, likely due to its high soluble expression and activity on formaldehyde. The combination of LmACR and RuHACL enabled the production of 6.2±0.6 mM glycolic acid in 1 hr. The use of 13C-labeled formaldehyde confirmed that the observed glycolic acid was derived from the C1 substrate, judging by the +2 shift in m/z of the $[M-15]^+$ ion (FIG. 13C).

Quantification of product and substrate concentrations (formic acid, formaldehyde, glycolic acid, ethylene glycol, ethanol, acetic acid) were determined via HPLC using a Shimadzu Prominence SIL 20 system (Shimadzu Scientific Instruments, Inc., Columbia, MD) equipped with a refractive index detector and an HPX-87H organic acid column (Bio-Rad, Hercules, CA) with operating conditions to optimize peak separation (0.3 ml/min flowrate, 30 mM $H_2SO_4$ mobile phase, column temperature 42° C.). Compound identification and analysis was performed by GC-MS using an Agilent 7890B Series Custom Gas Chromatography system equipped with a 5977B Inert Plus Mass Selective Detector Turbo EI Bundle (for identification) and an Agilent HP-5-ms capillary column (0.25 mm internal diameter, 0.25 µm film thickness, 30 m length).

To demonstrate the utility of the HACL-catalyzed elongation reaction for generating varied chemical functionalities from the resulting 2-hydroxyacyl-CoA product, we included enzymes to extend the LmACR+RuHACL pathway (FIG. 3a). An acyl-CoA reductase is needed to reduce glycolyl-CoA to glycolaldehyde, and upon screening the same set of ACRs for activity on glycolaldehyde, we found that LmACR was also able to act upon glycolaldehyde. To minimize the complexity of the engineered system, we used LmACR in a bifunctional role, catalyzing both the oxidation of formaldehyde to formyl-CoA and the reduction of glycolyl-CoA to glycolaldehyde. As shown in FIG. 13D, LmACR alone resulted in only the conversion of formaldehyde to formate. With the inclusion of RuHACL, glycolate was observed. Glycolaldehyde, however, was not significantly detected as a product, probably due to the presence of endogenous oxidoreductases in the cell extract system, which catalyzed the oxidation of glycolaldehyde to glycolic acid or, to a lesser extent, reduction to ethylene glycol.

The synthesis of the next reduction product, ethylene glycol, was significantly increased by the addition of a cell extract of *E. coli* overexpressing *E. coli* FucO, a 1,2-diol oxidoreductase (a 2-fold increase, from 1.37±0.1 mM to 2.73±0.03 mM) (FIG. 13D). Ethylene glycol can be further dehydrated to acetaldehyde by a diol dehydratase. Upon addition of *E. coli* cell extract expressing diol dehydratase (DDR) from *Klebsiella oxytoca*, ethanol was detected (1.90±0.03 mM at one hour: FIG. 13D), a product of the reduction of acetaldehyde by endogenous aldehyde reductases, along with a corresponding decrease in ethylene glycol. Synthesis of these varied products (i.e. glycolate, ethylene glycol, ethanol) illustrates the use of the 2-hydroxyacyl-CoA node to readily generate products at varying levels of reduction, chain lengths, and functionalities.

Figure 14:
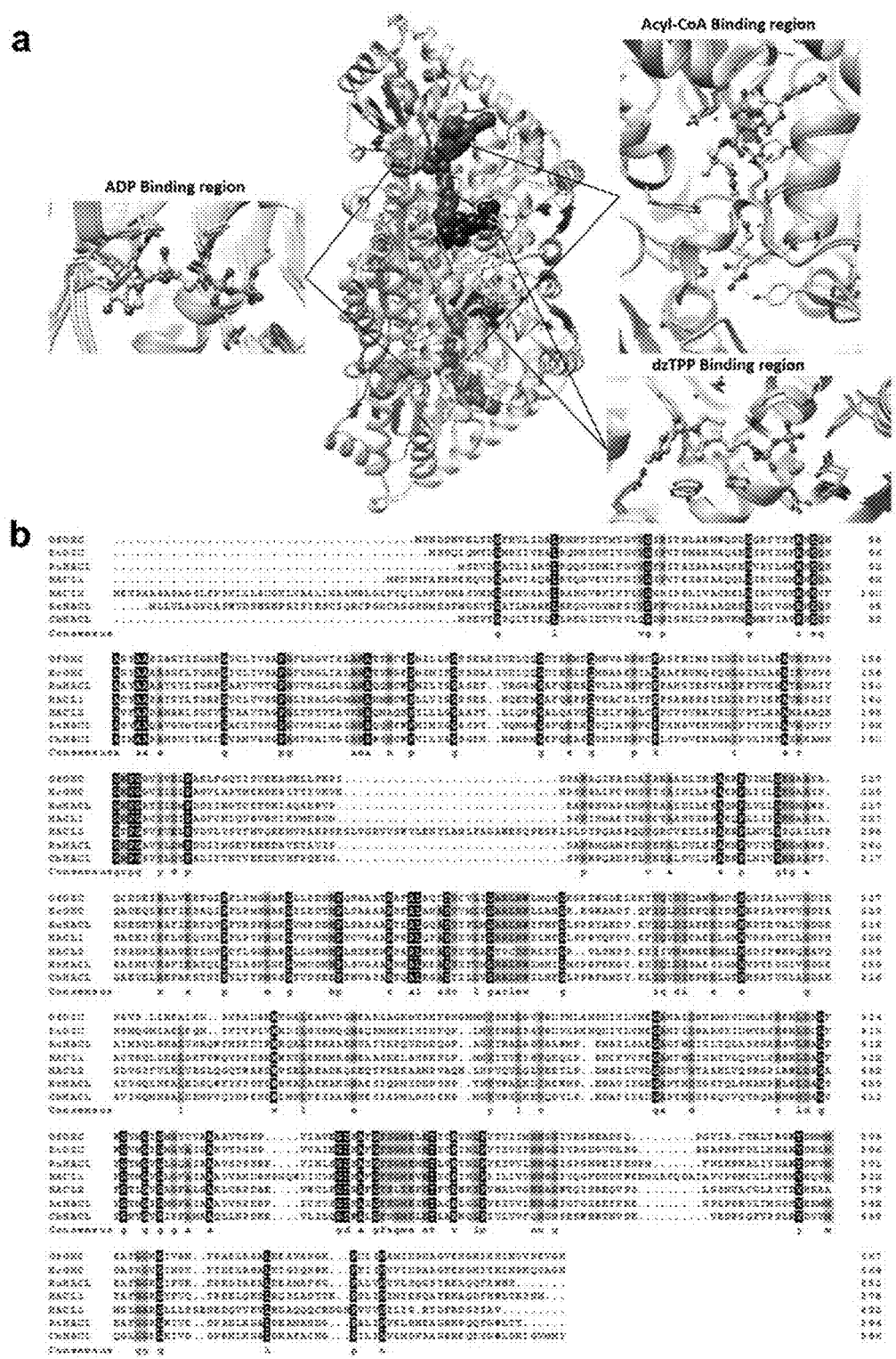
FIG. 14: Analysis of RuHACL sequence and structure by homology. a, Structure comparison of OfOxc with modeled RuHACL using SWISS-MODEL. Gold: OfOxc; Cyan: RuHACL. The cofactors and substrate molecules are shown as spheres and highlighted with different colors. Green: ADP; Red: oxalyl-CoA; Blue: dzTPP. The zoomed in figures show the cofactors and substrate binding information in the enzyme pockets, and all the residues involved in the binding are depicted as sticks, with the cofactors and substrates depicted as ball-and-stick models. b, Amino acid sequence alignment of OfOxc, EcOxc, RuHACL, HsHACL1, HsHACL2, RtHACL, and CbHACL.
Figure 15:
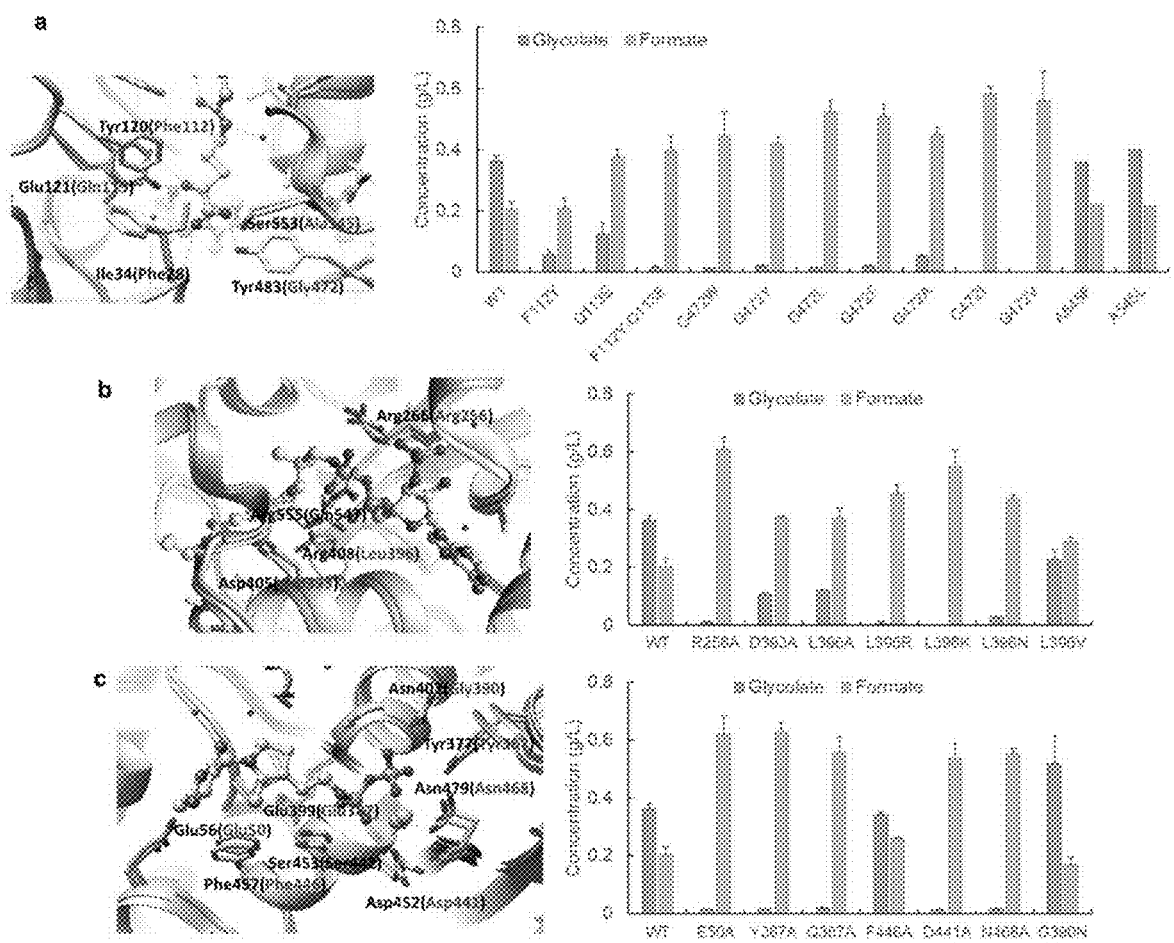
FIG. 15: Mutation of RuHACL substrate and cofactor binding regions. The predicted residues involved in binding are depicted as sticks and labeled with the corresponding amino acid and residue number in OfOxc. The corresponding residues from RuHACL are labeled in parentheses, and the residues queried in this study by mutation are indicated in red. a, (Left) Structure comparison of the oxalyl/glycolyl moiety binding pocket of OfOxc and modeled RuHACL. (Right) Bioconversion of formaldehyde to glycolate by expressing wild type (WT) RuHACL and RuHACL mutants with amino acid substitutions expected to impact acyl binding. b, (Left) Structure comparison of the CoA moiety binding pocket of OfOxc and modeled RuHACL. (Right) Bioconversion of formaldehyde to glycolate by expressing wild type (WT) RuHACL and RuHACL mutants with amino acid substitutions expected to impact CoA binding. c, (Left) Structure comparison of the TPP binding pocket of OfOxc and modeled RuHACL displaying the TPP analog 3-deazathiamin diphosphate (dzTPP). (Right) Bioconversion of formaldehyde to glycolate by expressing wild type (WT) RuHACL and RuHACL$^{G390N}$. Product concentrations are shown for 6 hr time points using 10 OD cells and 10 mM formaldehyde added at time 0 and 1.5 hrs.

Example 8: Homology-Guided Mutagenesis of Prokaryotic Enzymes Catalyzing TPP-Dependent Acyloin Condensation Reactions To obtain further insight on determinants of RuHACL activity, we analyzed the structure of RuHACL derived from homology modeling using SWISS-MODEL with OfOxc (PDB: 2ji6) as a template (FIG. 14A) along with sequence alignment information (FIG. 14B). Based on our analysis, we mutated selected residues that we believed might be important for the ability of RuHACL to catalyze the condensation of formaldehyde and formyl-CoA with the corresponding formation of glycolate. Because oxalyl-CoA is a two-carbon acyl-CoA similar to glycolyl-CoA, the product of the synthetic HACL reaction using formaldehyde, we used the binding of the oxalyl group in OfOxc as a guide to understand glycolyl binding in RuHACL (FIG. 15A). We observed that the amino acid substitutions F112Y and Q113E individually and in combination had a negative impact on bioconversion activity, as judged by a decrease in glycolate production (FIG. 15A). There was a clear distinction between the identities of these residues in the Oxc variants and the predicted HACL variants, where both OfOxc and EcOxc had tyrosine and glutamate in these positions and the HACL variants had consensus phenylalanine and glutamine (with the exception of HsHACL2, which has isoleucine in place of phenylalanine) (FIG. 14B). In light of the experimental results, it appears that these residues play an important role on the activity of HACL and could be useful in distinguishing between Oxc and HACL activities.

Residues Ser553 and Tyr483 in OfOxc interact with the carboxylate oxygen of the oxalyl group via hydrogen bond formation. These residues are replaced by amino acids with small side chains, Gly472 and Ala545 in RuHACL (FIG. 15A). We hypothesized that this is necessary to accommodate the larger alkyl chains of native HACL substrates, which would be in place of the carboxylate of oxalyl-CoA. In an attempt to reduce the empty space to improve glycolyl binding, we introduced bulky amino acids in these positions and tested various substitutions. Substitutions A545F and A545L did not significantly impact glycolate production, whereas all tested substitutions at G472 either partially or completely abolished it (FIG. 15A). It appears that the glycine in this position is critical to the function of RuHACL, which is unexpected given the simplicity of glycine.

In binding the substrate CoA group (FIG. 15B), we made, among other mutations, the substitution L396R in RuHACL in an attempt to match the consensus sequence and thus improve enzyme-substrate binding but were surprised to find that this abolished the production of glycolate in the biotransformation system (FIG. 15B). Furthermore, L396A and L396V substitutions were also found to reduce glycolate production. These results suggest the importance of a non-polar side chain at this position in RuHACL and its size appears to influence the ability of RuHACL to catalyze the condensation of formaldehyde and formyl-CoA, with leucine performing better than valine, which in turn was better than alanine. We also observed a potential consensus motif of (based on OfOxc positions) Ala264, Arg266, Asp405, and Arg408 across Oxc and HACL variants (again with the exception of HsHACL2) (Supplementary FIG. 8b). We mutated residue Arg256 of RuHACL, which is expected to hydrogen bond with the phosphate of the phosphoadenosine group, to alanine and observed the near abolishment of glycolate production, as expected (FIG. 15B). We also perturbed a nearby residue to the CoA binding region, Asp393, which is highly conserved in all HACL and OXC variants. We observed that the D393A mutant had reduced glycolate production, supporting the importance of this conserved residue on activity (FIG. 15B).

We further made the mutants Y367A, which is expected to interact with the diphosphate group of TPP, and Q387A and F446A, which are expected to interact with the thiamine group of TPP. The mutants Y367A and Q387A were detrimental to glycolate production, while F446A did not have a significant impact (FIG. 15C). Additionally, the mutants D441A and N468A were constructed. These residues are expected to assist in coordinating a Mg' ion with the diphosphate group of TPP, and the mutants displayed significantly reduced ability to produce glycolate.

TPP-dependent enzymes are known to have a catalytic glutamate residue that activates TPP. In RuHACL, this is expected to be the residue Glu50. We made an E50A mutant of RuHACL and confirmed that glycolate production was nearly abolished (FIG. 15C). This finding supports our hypothesized TPP-dependent mechanism for the acyloin condensation reaction between formyl-CoA and carbonyl-containing substrates catalyzed by HACL. We also made a G390N substitution in RuHACL to restore the consensus TPP binding sequence and found that this modification resulted in an increase in glycolate production (FIG. 15C). When implemented in the previously described biotransformation system, the strain expressing the mutant RuHACL$^{G390N}$ resulted in the production of 0.64 g/L glycolate in 24 hours, corresponding to an 84% yield. The use of mutant RuHACL$^{G390N}$ along with different strategies for formaldehyde addition and varying cell densities led to an increase in glycolate titers to over 1.2 g/L in 24 hrs. We further investigated the kinetics of the C1 condensation reaction using the G390N RuHACL mutant by measuring its kinetic parameters on formyl-CoA and formaldehyde and observed no significant difference in $k_{cat}$ or KM of the mutant compared to the wild type in the tested in vitro conditions. We hypothesize that rather than improve the kinetics of the reaction in relation to the substrates, the G390N mutation allows RuHACL to better bind and sequester free TPP which results in improved catalysis, especially under bioconversion conditions where only physiological quantities of TPP are available.

The following references are incorporated by reference in their entirety herein for all purposes.

Cheong, S., Clomburg, J. M. and Gonzalez, R., 2016. Energy- and carbon-efficient synthesis of functionalized small molecules in bacteria using non-decarboxylative Claisen condensation reactions. Nat. Biotechnol., 34(5), 556-561.

Clomburg, J. M., Vick, J. E., Blankschien, M. D., Rodriguez-Moyá, M. and Gonzalez, R., 2012. A synthetic biology approach to engineer a functional reversal of the β-oxidation cycle. ACS Synthetic Biology, 1(11), 541-554.

Goh, E. B., Baidoo, E. E., Burd, H., Lee, T. S., Keasling, J. D. and Beller, H. R., 2014. Substantial improvements in methyl ketone production in *E. coli* and insights on the pathway from in vitro studies. Metabolic engineering, 26, 67-76.

Kunjapur, A. M. and Prather, K. L., 2015. Microbial engineering for aldehyde synthesis. Appl. Environ. Microbiol., 81(6), 1892-1901.

Lindlbauer, K. A., Marx, H. and Sauer, M., 2017. 3-Hydroxypropionaldehyde production from crude glycerol by *Lactobacillus diolivorans* with enhanced glycerol uptake. Biotechnology for Biofuels, 10(1), 295.

Neidhardt, F. C., Bloch, P. L. and Smith, D. F., 1974. Culture medium for enterobacteria. J. Bacteriol., 119(3), 736-747.

Park, J., Rodriguez-Moyá, M., Li, M., Pichersky, E., San, K. Y. and Gonzalez, R., 2012. Synthesis of methyl ketones by metabolically engineered *Escherichia coli*. J. Ind. Microbiol. Biotechnol., 39(11), 1703-1712.

Rodriguez, G. M. and Atsumi, S., 2012. Isobutyraldehyde production from *Escherichia coli* by removing aldehyde reductase activity. Microbial Cell Factories, 11(1), 90.

Srirangan, K., Liu, X., Akawi, L., Bruder, M., Moo-Young, M. and Chou, C. P., 2016. Engineering *Escherichia coli* for microbial production of butanone. Appl. Environ. Microbiol., 82(9), 2574-2584.

Unless otherwise indicated, all numbers expressing reaction conditions, quantities of ingredients, and so forth, as used in this specification and the claims are to be understood as being modified in all instances by the term "about." While this invention has been particularly shown and described with references to preferred embodiments thereof, it will be understood by those skilled in the art that various changes in form and details may be made therein without departing from the scope of the invention encompassed by the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference. The relevant teachings of all patents, published applications and references cited herein are incorporated by reference in their entirety.

What is claimed is:

1. A method for the production of an alpha-branched 2-hydroxyacyl-CoA comprising condensation of a formyl-CoA with a ketone; wherein the condensation is catalyzed by a TPP-dependent enzyme, wherein the alpha-branched 2-hydroxyacyl CoA is one carbon longer than the ketone, wherein the TPP-dependent enzyme is selected from the group consisting of 2-hydroxyacyl-CoA lyase (HACL), oxalyl-CoA decarboxylase and benzaldehyde lyase.

2. The method of claim 1, wherein the TPP-dependent enzyme is a 2-hydroxyacyl-CoA lyase (HACL).

3. The method of claim 1, further comprising producing the formyl-CoA by contacting a one-carbon substrate with an enzyme catalyst, wherein the one-carbon substrate is selected from the group consisting of methane, methanol, formate, formaldehyde and carbon dioxide.

4. The method of claim 1, further comprising producing the ketone by contacting a substrate with an enzyme catalyst.

5. The method of claim 1, further comprising converting the alpha-branched 2-hydroxyacyl-CoA to a branched product.

6. The method of claim 3, wherein the one-carbon substrate is formaldehyde and the enzyme catalyst that produces the formyl-CoA is:
   a. an acyl-CoA reductase (acylating aldehyde dehydrogenase) that catalyzes the conversion of the formaldehyde to the formyl-CoA.

7. The method of claim 3, wherein the one-carbon substrate is methanol and the enzyme catalysts to produce the formyl-CoA are:
   a. a methanol dehydrogenase catalyzing the conversion of the methanol to formaldehyde; and
   b. an acyl-CoA reductase (acylating aldehyde dehydrogenase) catalyzing the conversion of the formaldehyde to the formyl-CoA.

8. The method of claim 3, wherein the one-carbon substrate is methane and the enzyme catalysts to produce the formyl-CoA are:
   a. a methane monooxygenase catalyzing the conversion of the methane to methanol;
   b. a methanol dehydrogenase catalyzing the conversion of the methanol to formaldehyde; and
   c. an acyl-CoA reductase (acylating aldehyde dehydrogenase) catalyzing the conversion of the formaldehyde to formyl-CoA.

9. The method of claim 3, wherein the one-carbon substrate is formate and the enzyme catalysts to produce the formyl-CoA are:
   a. an acyl-CoA synthase catalyzing the conversion of the formate to formyl-CoA; or
   b. a formate kinase catalyzing the conversion of the formate to formyl-phosphate and a phosphate formyl-transferase catalyzing the conversion of formyl-phosphate to the formyl-CoA.

10. The method of claim 3, wherein the one-carbon substrate is carbon dioxide and the enzyme catalysts to produce the formyl-CoA are:
    a. a carbon dioxide reductase catalyzing the conversion of the carbon dioxide to formate; and
    b. an acyl-CoA synthase catalyzing the conversion of the formate to the formyl-CoA; or
    c. a formate kinase catalyzing the conversion of formate to formyl-phosphate and a phosphate formyl-transferase catalyzing the conversion of formyl-phosphate to the formyl-CoA.

11. The method of claim 5, wherein the branched product is a branched aldehyde, wherein the conversion of the alpha-branched 2-hydroxyacyl-CoA to said product is catalyzed by an enzyme catalyst, and wherein the enzyme catalyst is:
    a. an acyl-CoA reductase catalyzing the conversion of the alpha-branched 2-hydroxyacyl-CoA to the branched aldehyde.

12. The method of claim 5, wherein the alpha-branched product is a branched alcohol, wherein the conversion of the alpha-branched 2-hydroxyacyl-CoA to said branched product is catalyzed by enzyme catalysts, and wherein the enzyme catalysts are:

a. an acyl-CoA reductase catalyzing the conversion of the alpha-branched 2-hydroxyacyl-CoA to the branched aldehyde; and
b. an alcohol dehydrogenase (aldehyde reductase) catalyzing the conversion of the branched aldehyde to the branched alcohol.

13. The method of claim 5, wherein the product is a branched carboxylic acid, wherein the conversion of the alpha-branched 2-hydroxyacyl-CoA to said product is catalyzed by enzyme catalysts, and wherein the enzyme catalysts are:
a. a thioesterase catalyzing the conversion of the branched 2-hydroxyacyl-CoA to the branched carboxylic acid.

14. The method of claim 3, wherein the enzyme catalysts are contained in a recombinant microorganism harboring the genes for expressing each enzyme.

15. The method of claim 3, wherein the substrates are contacted with enzyme catalysts by addition of each to an aqueous reaction mixture optionally containing buffers, salts, vitamins, minerals, and cofactors.

16. The method of claim 2, wherein the 2-hydroxacyl-CoA lyase is a human HACL.

17. The method of claim 16, wherein the human HACL is *Homo sapiens* HACL1.

18. The method of claim 2, wherein the 2-hydroxyacyl-CoA lyase is a prokaryotic HACL.

19. The method of claim 18, wherein the prokaryotic HACL is from Rhodospiralles bacterium URHD0017.

20. The method of claim 1, wherein the ketone is a methyl ketone.

21. The method of claim 20, wherein the methyl ketone has the formula:

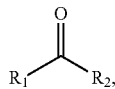

wherein $R_1$ is methyl, and $R_2$ is an alkyl; and
the alpha-branched 2-hydroxyacyl-CoA has the formula:

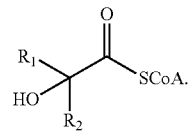

22. The method of claim 21, wherein $R_2$ is selected from the group consisting of methyl, ethyl and propyl.

23. The method of claim 22, wherein the ketone is acetone.

24. The method of claim 22, wherein the ketone is 2-butanone.

25. The method of claim 22, wherein the ketone is 2-pentanone.

26. The method of claim 1, wherein the ketone is 3-pentanone and the alpha-branched 2-hydroxyacyl CoA is

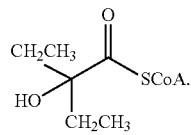

27. The method of claim 1, wherein the ketone is hydroxyacetone and the alpha-branched 2-hydroxyacyl-CoA is 2,3-dihydroxyisobutyryl-CoA.

* * * * *